US007829316B2

(12) United States Patent
Koseki et al.

(10) Patent No.: US 7,829,316 B2

(45) Date of Patent: Nov. 9, 2010

(54) PROCESS FOR PRODUCTION OF SUCCINIC ACID

(75) Inventors: Chie Koseki, Kawasaki (JP); Keita Fukui, Kawasaki (JP); Jun Nakamura, Kawasaki (JP); Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/104,595

(22) Filed: Apr. 17, 2008

(65) Prior Publication Data

US 2008/0293113 A1 Nov. 27, 2008

Related U.S. Application Data

(63) Continuation of application No. PCT/JP2006/320675, filed on Oct. 17, 2006.

(30) Foreign Application Priority Data

Oct. 18, 2005 (JP) ............................ 2005-303213

(51) Int. Cl.

| | |
|---|---|
| *C12P 7/46* | (2006.01) |
| *C12N 9/04* | (2006.01) |
| *C12N 15/00* | (2006.01) |
| *C12N 15/74* | (2006.01) |
| *C12N 1/20* | (2006.01) |
| *C12Q 1/32* | (2006.01) |
| *C07H 21/04* | (2006.01) |

(52) U.S. Cl. ......................... 435/145; 435/190; 435/26; 435/455; 435/471; 435/320.1; 435/252.3; 435/252.31; 435/252.32; 536/23.7

(58) Field of Classification Search ................. 435/145, 435/190, 455, 471, 26, 320.1, 252.3, 252.31, 435/252.32; 536/23.7

See application file for complete search history.

(56) References Cited

U.S. PATENT DOCUMENTS

| | | | | |
|---|---|---|---|---|
| 5,034,105 | A | 7/1991 | Berglund et al. | |
| 5,132,456 | A | 7/1992 | King et al. | |
| 5,142,834 | A | 9/1992 | Laclave et al. | |
| 5,143,833 | A | 9/1992 | Datta | |
| 5,143,834 | A | 9/1992 | Glassner et al. | |
| 5,168,055 | A | 12/1992 | Datta et al. | |
| 5,504,004 | A | 4/1996 | Guettler et al. | |
| 5,770,435 | A | 6/1998 | Donnelly et al. | |
| 5,827,700 | A | 10/1998 | Felman et al. | |
| 5,869,301 | A | 2/1999 | Nghiem et al. | |
| 5,958,744 | A | 9/1999 | Berglund et al. | |
| 6,265,190 | B1 | 7/2001 | Yedur et al. | |
| 6,448,061 | B1 | 9/2002 | Pan et al. | |
| 6,455,284 | B1 | 9/2002 | Gokarn et al. | |
| 6,696,561 | B1 * | 2/2004 | Pompejus et al. | 536/23.7 |
| 7,273,721 | B2 * | 9/2007 | Pompejus et al. | 435/41 |
| 2002/0150999 | A1 | 10/2002 | Dusch et al. | |
| 2002/0197605 | A1 | 12/2002 | Nakagawa et al. | |
| 2003/0017559 | A1 | 1/2003 | Donnelly et al. | |
| 2003/0069354 | A1 | 4/2003 | Oyasato et al. | |
| 2003/0087381 | A1 | 5/2003 | Gokarn et al. | |
| 2003/0100079 | A1 | 5/2003 | Mockel et al. | |
| 2005/0196848 | A1 | 9/2005 | Dusch et al. | |
| 2006/0172401 | A1 | 8/2006 | Yamagishi | |
| 2006/0205048 | A1 | 9/2006 | Murase et al. | |
| 2006/0228712 | A1 | 10/2006 | Nakagawa et al. | |
| 2006/0276674 | A1 | 12/2006 | Kushiku et al. | |
| 2006/0281156 | A1 | 12/2006 | Aoyama et al. | |
| 2007/0154999 | A1 | 7/2007 | Fukui et al. | |

FOREIGN PATENT DOCUMENTS

| | | |
|---|---|---|
| CA | 2322553 | 4/2001 |
| EP | 0389103 | 9/1990 |
| EP | 0410728 | 1/1991 |
| EP | 1096013 | 5/2001 |
| EP | 1108790 | 6/2001 |
| EP | 1 647 594 A1 | 4/2006 |
| EP | 1748062 | 1/2007 |
| JP | 61-209596 | 9/1986 |
| JP | 62-048394 | 3/1987 |
| JP | 62-238231 | 10/1987 |
| JP | 62-238232 | 10/1987 |
| JP | 62-294090 | 12/1987 |
| JP | 2-283289 | 11/1990 |
| JP | 3-072891 | 3/1991 |
| JP | 3-151884 | 6/1991 |
| JP | 5-260985 | 10/1993 |

(Continued)

OTHER PUBLICATIONS

Song et al., Production of succinic acid by bacterial fermentation. Enzyme Microbial Technol., 2006, vol. 39: 352-261.*

Broun et al., Catalytic plasticity of fatty acid modification enzymes underlying chemical diversity of plant lipids. Science, 1998, vol. 282: 1315-1317.*

Devos et al., Practical limits of function prediction: Proteins: Structure, function, and Genetics, 2000, vol. 41: 98-107.*

Guo et al., Protein tolerance to random amino acid change. PNAS., 2004, vol. 101 (25): 9205-9210.*

Seffernick et al., Melamine deaminase and Atrazine chlorohydrolase: 98 percent identical but functionally different. J. Bacteriol., 2001, vol. 183 (8): 2405-2410.*

(Continued)

*Primary Examiner*—Ganapathirama Raghu

(74) *Attorney, Agent, or Firm*—Greenblum & Bernstein, P.L.C.

(57) ABSTRACT

Disclosed is a process for production of succinic acid, which comprises the step of reacting a bacterium which has been modified so as to increase the expression of a sucE1 gene or a product produced by any treatment of the bacterium with an organic raw material in a reaction solution containing a carbonate ion, a bicarbonate ion or carbon dioxide gas to thereby yield the desired succinic acid.

5 Claims, 4 Drawing Sheets

FOREIGN PATENT DOCUMENTS

| | | | |
|---|---|---|---|
| JP | 6-14781 | | 1/1994 |
| JP | 7-67683 | | 3/1995 |
| JP | 7-304839 | | 11/1995 |
| JP | 11-113588 | | 4/1999 |
| JP | 11-130852 | | 5/1999 |
| JP | 11-196887 | | 7/1999 |
| JP | 11-196888 | | 7/1999 |
| JP | 11-206385 | | 8/1999 |
| JP | 2000-500333 | | 1/2000 |
| JP | 2000-037196 | | 2/2000 |
| JP | 2001-161386 | | 6/2001 |
| JP | 2001-190297 | | 7/2001 |
| JP | 2001-514900 | | 9/2001 |
| JP | 2002-511250 | | 4/2002 |
| JP | 2002-191370 | | 7/2002 |
| JP | 2002-291477 | | 10/2002 |
| JP | 2003-171448 | | 6/2003 |
| JP | 2003-199522 | | 7/2003 |
| JP | 2003-235592 | | 8/2003 |
| JP | 2003-235593 | | 8/2003 |
| JP | 2006-320278 | A | 11/2006 |
| WO | 97/16528 | | 5/1997 |
| WO | 99/06532 | | 2/1999 |
| WO | 99/09196 | | 2/1999 |
| WO | 99/53035 | | 10/1999 |
| WO | 01/00844 | A2 | 1/2001 |
| WO | 01/00844 | A3 | 1/2001 |
| WO | 01/66508 | | 9/2001 |
| WO | 02/29020 | | 4/2002 |
| WO | 02/36797 | | 5/2002 |
| WO | 02/072855 | | 9/2002 |
| WO | 03/040290 | | 5/2003 |
| WO | 2005/005649 | | 1/2005 |
| WO | 2005/021770 | | 3/2005 |
| WO | 2005/026349 | | 3/2005 |
| WO | 2005/030973 | | 4/2005 |
| WO | 2005/113744 | | 12/2005 |
| WO | 2005/113745 | | 12/2005 |
| WO | 2007/046389 | | 4/2007 |

OTHER PUBLICATIONS

Whisstock et al., Prediction of protein function from protein sequence. Q. Rev. Biophysics., 2003, vol. 36 (3): 307-340.*

Witkowski et al., Conversion of b-ketoacyl synthase to a Malonyl Decarboxylase by replacement of the active cysteine with glutamine. Biochemistry, 1999, vol. 38: 11643-11650.*

Current Protocols in Molecular Biology, (1993) 2.10.0-2.10.16; Copyright 2000 by John Wiley & Sons, Inc.*

U.S. Appl. No. 11/561,011 (Fukui et al.), filed Nov. 17, 2006.

U.S. Appl. No. 12/090,431 (Koseki et al.), filed Apr. 16, 2008.

English Language Abstract of JP 3-072891, Mar. 28, 1991.

English Language Abstract of JP 5-260985, Oct. 12, 1993.

English Language Abstract of JP 6-014781, Jan. 25, 1994.

English Language Abstract of JP 7-67683, Mar. 14, 1995.

English Language Abstract of JP 7-304839, Nov. 21, 1995.

English Language Abstract of 11-113588, Apr. 27, 1999.

English Language Abstract of JP 11-130852, May 18, 1999.

English Language Abstract and Computer Translation of JP 11-196887, Jul. 27, 1999.

English Language Abstract of JP 11-196888, Jul. 27, 1999.

English Language Abstract of JP 11-206385, Aug. 3, 1999.

English Language Abstract of JP 61-209596, Sep. 17, 1986.

English Language Abstract of JP 62-048394, Mar. 3, 1987.

English Language Abstract of JP 62-238231, Oct. 19, 1987.

English Language Abstract of JP 62-238232, Oct. 19, 1987.

English Language Abstract of JP 2000-037196, Feb. 8, 2000.

English Language Abstract of JP 2001-161386, Jun. 19, 2001.

English Language Abstract of JP 2001-190297, Jul. 17, 2001.

English Language Abstract of JP 2002-191370, Jul. 9, 2002.

English Language Abstract and Computer Translation of JP2002-291447, Oct. 8, 2002.

English Language Abstract of JP 2003-171448, Jun. 20, 2003.

English Language Abstract of JP 2003-199522, Jul. 15, 2003.

English Language Abstract of JP 2003-235592, Aug. 26, 2003.

English Language Abstract and Computer Translation of JP2003-235593, Aug. 26, 2003.

Ba et al. *Biomacromolecules* 4: 1827-1834, 2003.

Bott et al. *Journal of Biotechnology* 104:129-153, 2003.

Branden et al. *Introduction to Protein Structure*, Garland Publishing Inc., New York, p. 247, 1991.

Calvary et al. *Microchemical Journal* 23(4):473-480, 1978.

Chotani et al. *Biochimica et Biophysica Acta, Protein Structure and Molecular Enzymology* 1543(2):434-455, 2000.

Database UniProt, Accession No. Q8NMK4, Oct. 1, 2002.

Database EPO Proteins, Accession No. AX771820, Jul. 2, 2003.

Database EMBL, Accession No. AX771819, Jul. 2, 2003.

Database Geneseq, Accession No. AAG92572, Sep. 26, 2001.

Database EMBL, Accession No. AX122910, May 10, 2001.

Database UniProt, Accession No. Q6M2R3, Jul. 5, 2004.

Gokarn et al. *Biotechnology Letters* 20(8): 795-798, 1998.

Gokarn et al. *Applied and Environmental Microbiology* 66(5):1844-1850, 2000.

Gokarn et al. *Appl. Microbiol. Biotechnol.* 56:188-195, 2001.

Goldberg et al. *Applied and Environmental Microbiology* 45(6): 1838-1847, 1983.

Gong et al. *Applied Biochemistry and Biotechnology* 57/58:481-487, 1996.

Guettler et al. *International Journal of Systematic Bacteriology* 49:207-216, 1999.

Hong et al. *Biotechnology and Bioengineering* 74(2):89-95, 2001.

Hong et al. *Applied Microbiology and Biotechnology* 58:286-290, 2002.

Inui et al. *J. of Mol. Microbiol. and Biotechnol.* 7(4):182-196, 2004.

Kalinowski et al. *J. of Biotech.* 104(1-3):5-25, 2003.

KEGG Database on-line, NCg10359, 2006.

KEGG Database on-line, NCg10360, 2006.

KEGG Database on-line, NCg10361, 2006.

Kirchner et al. *J. of Biotech.* 104(1-3):287-299, 2003.

Kurokawa et al. *Arch. Microbiol.* 183:317-324, 2005.

Lin et al. *Applied Genetics and Molecular Biotechnology*, published online: Nov. 24, 2004, total pages: 16.

Mat-Jan et al. *Journal of Bacteriology* 171(1):342-348, 1989.

Maxa et al. *Mitteilungen Klosterneuburg* 41(6):233-237, 1991.

Millard et al. *Applied and Environmental Microbiology* 62(5):1808-1810, 1996.

Mori et al. *Shokuhin to Kagaku* 44(4):43-49, 2002.

NP_601767, NCBI Sequence Viewer, Acetyl-CoA hydrolase, Dec. 14, 2006.

NP_601811, NCBI Sequence Viewer, Pyruvate Dehyrogenase, Dec. 14, 2006.

Reinscheid et al. *Microbiology* 145:503-513, 1999.

Schnorpfeil et al. *Eur. J. Biochem.* 268:3069-3074, 2001.

Seffernick et al. *J. Bacteriol.* 183(8): 2405-2410, 2001.

Stols et al. *Applied and Environmental Microbiology* 63(7):2695-2701, 1997.

Wang et al. *Applied Biochemistry and Biotechnology* 70-72:919-928, 1998.

Witkowski et al. *Biochemistry* 38:11643-11650, 1999.

Zeikus et al. *Appl. Microbiol. Biotechnol.* 51:545-552, 1999.

Ikeda M. et al., "The *Corynebacterium glutamicum* genome: features and impacts on biotechnological processes" Appl. Microbiol. Biotechnol., vol. 62, No. 2-3, p. 99-109, 2003.

International Search Report for PCT/JP2006/320675, mailed Jan. 9. 2007.

International Preliminary Report on Patentability for PCT/JP2006/320675, mailed Sep. 18, 2008.

* cited by examiner

PROCESS FOR PRODUCTION OF SUCCINIC ACID

The present application is a Continuation of International Patent Application No. PCT/JP2006/320675 filed on Oct. 17, 2006, and claims priority under 35 U.S.C. §119 of Japanese Patent Application No. 2005-303213, filed on Oct. 18, 2005, the contents of which are expressly incorporated by reference herein in their entirety.

TECHNICAL FIELD

The present invention relates to production of succinic acid using bacteria such as coryneform bacteria.

BACKGROUND ART

For production of non-amino-organic acids including succinic acid by fermentation, usually, anaerobic bacteria such as those of the genera *Anaerobiospirillum* and *Actinobacillus* are used (Patent Document 1 and Patent Document 2, and Non Patent Document 1). The use of anaerobic bacteria makes yields of products high, while demanding many nutrients for proliferation of the bacteria. Therefore, there is a need of adding a large amount of an organic nitrogen source such as corn steep liquor (CSL) in a medium. The addition of abundant organic nitrogen source not only leads to an increase in cost of the medium but also leads to an increase in cost of purification for isolating the product, thereby being uneconomical.

In addition, methods, where aerobic bacteria such as coryneform bacteria are cultured under aerobic conditions to proliferate bacterial cells and then cells are harvested and washed to allow the cells as resting bacteria to produce non-amino organic acid without oxygen aeration, have been known in the art (Patent Document 3 and Patent Document 4). These methods are economical because the amount of organic nitrogen to be added for proliferating bacterial cells may be small and can proliferate cells sufficiently in a simple medium, but are susceptible to improvement in terms of the production amount of the organic acid of interest, the concentration thereof, and the production rate thereof per bacterial cell as well as simplification of the production process, and so on. Further, the production of non-amino organic acid by fermentation using a bacterium having an enhanced phosphoenol pyruvate carboxylase activity has also been reported (e.g., Patent Document 5).

The whole genome sequences of a coryneform bacterium have been identified to predict the functions of putative protein-coding sequences in the sequences (Non Patent Document 2). The gene referred to as sucE1 in the present invention is one of them and is predicted to encode permease. However, the actual functions of the gene have not been elucidated, and the involvement of the gene in a succinic acid synthetic pathway has been unknown yet.

Patent Document 1: U.S. Pat. No. 5,142,834 A

Patent Document 2: U.S. Pat. No. 5,504,004 A

Patent Document 3: JP 11-113588 A

Patent Document 4: JP 11-196888 A

Patent Document 5: JP 11-196887 A

Non Patent Document 1: International Journal of Systematic Bacteriology (1999), 49, 207-216

Non Patent Document 2: Appl. Microbiol. Biotechnol. 62(2-3), 99-109 (2003)

DISCLOSURE OF THE INVENTION

An object of the present invention is to provide a process for producing succinic acid with high production efficiency.

The inventors of the present invention have intensively investigated for solving the above-mentioned problems and accomplished the present invention by finding that consumption rate of organic raw materials, production rate of succinic acid, or yield thereof can be increased by allowing bacteria being modified so as to enhance the expression of a sucE1 gene or treated cells thereof to act on an organic raw material in a reaction solution containing carbonate ion, bicarbonate ion, or carbon dioxide gas.

According to the present invention, the following inventions are provided:

(1) A method for producing succinic acid, comprising: allowing a bacterium which is modified so that expression of a sucE1 gene is enhanced or treated cells thereof to act on an organic raw material in a reaction solution containing carbonate ion, bicarbonate ion, or carbon dioxide, to produce succinic acid; and collecting the succinic acid.

(2) The method according to (1), wherein the bacterium is selected from the group consisting of coryneform bacterium, *Bacillus* bacterium, and *Rhizobium* bacterium.

(3) The method according to (1) or (2), wherein the bacterium is modified so that expression of the sucE1 gene is enhanced by increasing the copy number of the gene or by modifying an expression regulatory sequence of the gene.

(4) The method according to any one of (1) to (3), wherein the sucE1 gene is a DNA as shown in (a) or (b):

(a) a DNA comprising the nucleotide sequence of nucleotide numbers 571 to 2,187 of SEQ ID NO: 15; or (b) a DNA which hybridizes with a sequence complementary to the nucleotide sequence of nucleotide numbers 571 to 2,187 of SEQ ID NO: 15 under stringent conditions and improves succinic acid-producing ability of a bacterium by enhancing expression of the gene in the bacterium.

(5) The method according to any one of (1) to (4), wherein the bacterium is further modified so that lactate dehydrogenase activity is decreased to 10% or less as compared to an unmodified strain.

(6) The method according to any one of (1) to (5), wherein the bacterium is further modified so that pyruvate carboxylase activity is enhanced.

(7) A method for producing a succinic acid-containing polymer, comprising the steps of: producing succinic acid by the method according to any one of (1) to (6); and polymerizing the obtained succinic acid.

DESCRIPTION OF THE PREFERRED EMBODIMENTS

Figure 1:
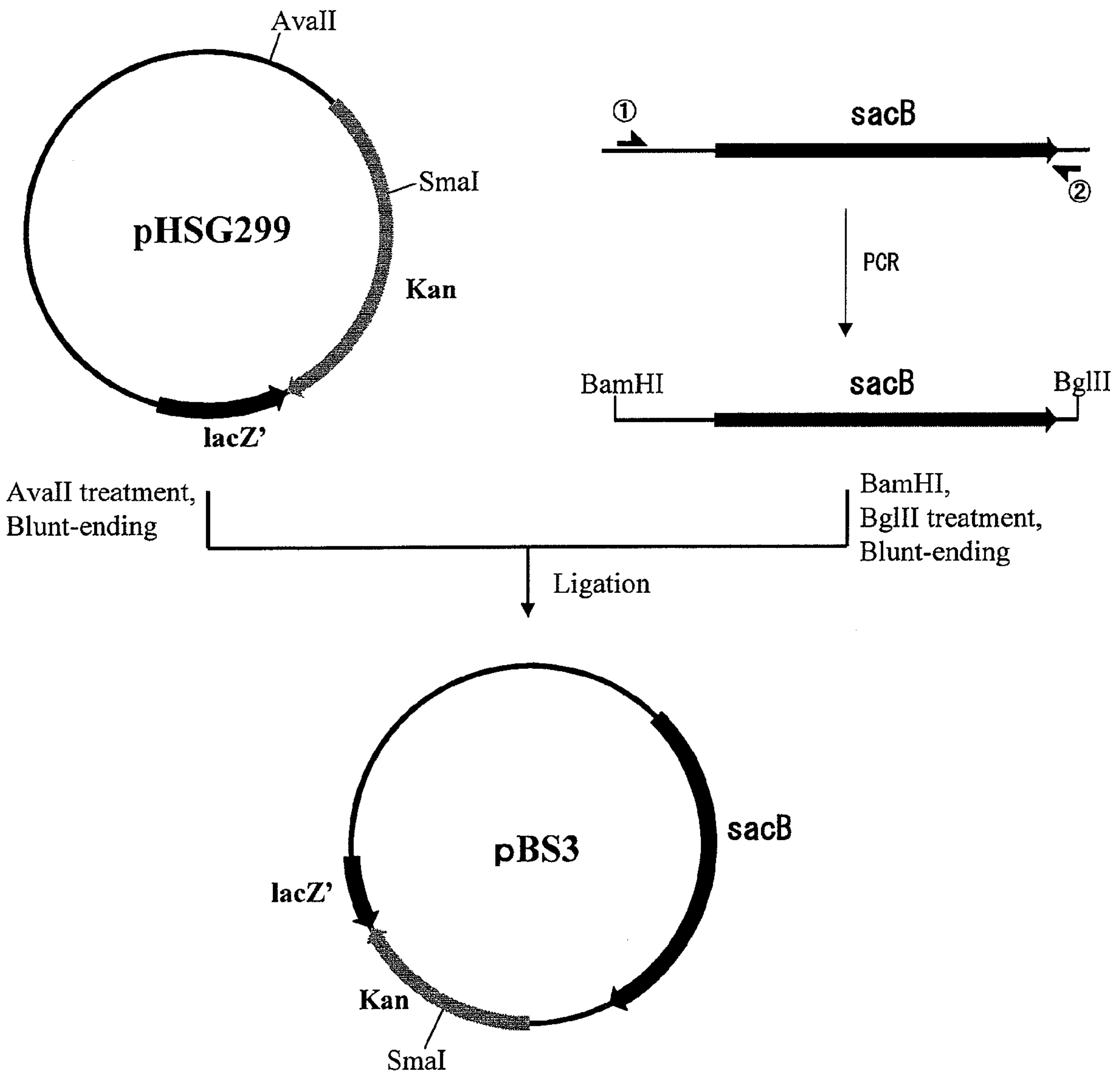
FIG. 1 A drawing showing the construction of the plasmid pBS3 for gene disruption. The numbers in the circles show the SEQ ID NOs of the primers.

Hereinafter, embodiments of the present invention will be described in detail.

The bacterium to be used in the present invention is one having succinic acid-producing ability and modified so that expression of a sucE1 gene is enhanced. Such a bacterium can be obtained by modifying a parent strain having succinic acid-producing ability so that expression of a sucE1 gene is enhanced. Meanwhile, in the case of using a parent strain that does not have succinic acid-producing ability, the bacterium can be obtained by imparting succinic acid-producing ability and modifying so that expression of a sucE1 gene is enhanced A parent strain of the bacterium that can be used in the present invention is not particularly limited. However, coryneform bacteria, *Bacillus* bacteria, *Rhizobium* bacteria, and *Escherichia* bacteria are preferable. Of these, coryneform bacteria are more preferable. Examples of the coryneform bacteria include a microorganism belonging to the genus *Corynebacterium*, a microorganism belonging to the genus *Brevibacterium*, and a microorganism belonging to the genus *Arthrobacter*. Of these, bacteria belonging to the genus *Corynebacterium* or *Brevibacterium* are preferable. More preferable are bacteria belonging to *Corynebacterium glutamicum, Brevibacterium flavum, Brevibacterium ammoniagenes*, or *Brevibacterium lactofermentum.*

Particularly preferable examples of the parent strain of the bacterium include *Brevibacterium flavum* MJ-233 (FERM BP-1497), *Brevibacterium flavum* MJ-233 AB-41 (FERM BP-1498), *Brevibacterium ammoniagenes* ATCC6872, *Corynebacterium glutamicum* ATCC31831, ATCC13032, and *Brevibacterium lactofermentum* ATCC13869. *Brevibacterium flavum* is currently classified into *Corynebacterium glutamicum* in some cases (Lielbl, W., Ehrmann, M., Ludwig, W. and Schleifer, K. H., International Journal of Systematic Bacteriology, 1991, vol. 41, p 255-260). Therefore, in the present invention, the *Brevibacterium flavum* MJ-233 strain and its mutant MJ-233 AB-41 strain are defined as the same strains as the *Corynebacterium glutamicum* MJ-233 strain and the *Corynebacterium glutamicum* MJ-233 AB-41 strain, respectively.

*Brevibacterium flavum* MJ-233 was deposited as the accession number FERM P-3068 at National Institute of Bioscience and Human Technology, Agency of Industrial Science and Technology, Ministry of International Trade and Industry (currently International Patent Organism Depositary, National Institute of Advanced Industrial Science and Technology at Central 6, 1-1, Higashi 1-chome, Tsukuba-shi, Ibaraki-ken 305-8566, Japan) on Apr. 28, 1975, and then converted to an international deposit under Budapest Treaty on May 1, 1981 with the accession number FERM BP-1497.

The bacteria to be used as a parent strain for obtaining the bacterium used in the method of the present invention may be any of strains including mutant strains obtained by general mutation treatments such as UV irradiation and NTG treatment, and recombinant strains induced by genetic procedures such as cell fusion and gene recombination techniques, as well as wild-type strains.

In the case of using a parent strain which does not have succinic acid-producing ability, the succinic acid-producing ability is imparted by mutation treatment or gene recombination. However, when succinic acid-producing ability is imparted by modification to enhance the expression of a sucE1 gene, it is not always necessary to impart the succinic acid-producing ability.

The term "succinic acid-producing ability" used herein refers to an ability of accumulating succinic acid in a medium to such an extent that the succinic acid is collected when the bacterium is cultured in the medium.

As a method of imparting or enhancing the succinic acid-producing ability by breeding, there is exemplified a method of modifying a bacterium so that expression of a gene encoding an enzyme involved in succinic acid biosynthesis is enhanced. Examples of the enzyme involved in succinic acid biosynthesis include a pyruvate carboxylase as described later and a fumarate reductase as disclosed in JP 2005-095169. Bacteria having enhanced pyruvate carboxylase and fumarate reductase genes are described in JP 2002-511250 A, JP 11-196888 A, JP 2005-95169 A, etc.

The modification for imparting the succinic acid-producing ability can be achieved by disrupting a gene encoding a lactate dehydrogenase, which is an enzyme that can be expressed under anaerobic conditions as described later. Meanwhile, the succinic acid-producing ability may be imparted by a method including: treating a bacterium with ultraviolet ray or with a mutagen to be used for a general mutation treatment such as N-methyl-N'-nitro-N-nitrosoguanidine (NTG) or ethylmethanesulfonate (EMS); and selecting a strain capable of producing succinic acid. An example of the mutant capable of producing succinic acid includes a glutamic acid-auxotrophic strain as disclosed in JP 2005-065641 A.

A bacterium to be used in the method of the present invention can be obtained by modifying a bacterium having succinic acid-producing ability as described above so that expression of a sucE1 gene is enhanced. There is no preference between the modification for imparting the succinic acid-producing ability and the modification for enhancing the expression of a sucE1 gene.

A protein encoded by a sucE1 gene (sucE; succinate exporter) is predicted to be a kind of permease and is a protein capable of improving "the succinic acid-producing ability" of a bacterium when the expression of the gene is enhanced in the bacterium.

Examples of the sucE1 gene to be used for obtaining a bacterium used in the method of the present invention include a sucE1 gene derived from *Brevibacterium flavum* MJ-233 (nucleotide numbers 571 to 2187 of SEQ ID NO: 15), a sucE1 gene derived from *C. glutamicum* ATCC13032 (nucleotide sequence of SEQ ID NO: 17), a sucE1 gene derived from *C. efficiens* YS314 (nucleotide sequence of SEQ ID NO: 19), and a sucE1 gene derived from *C. diphtheriae gravis* NCTC13129 (nucleotide sequence of SEQ ID NO: 23). The sucE1 gene derived from *C. glutamicum* ATCC13032 is deposited as NCgl2130 in the genome sequence deposited as GenBank Accession No. NC#003450 (amino acid sequence is deposited as GenBank Accession No. NP#601414). The sucE1 gene derived from *C. efficiens* YS314 is deposited as CE2102 in the genome sequence deposited as GenBank Accession No. NC#004369. The sucE1 gene derived from *C. diphtheriae gravis* NCTC13129 is deposited as DIP0830 of GenBank Accession No. NC#002935.

Meanwhile, a sucE1 gene to be used for obtaining a bacterium used in the method of the present invention may be a homologue gene of sucE1 derived from another microorganism as long as being capable of improving succinic acid-producing ability of the bacterium by enhancing the expression in the bacterium. The homologue of a sucE1 gene may be searched by BLAST (//blast.genome.jp/) or the like with reference to the sequence of nucleotide numbers 571 to 2187 of SEQ ID NO: 15.

As described above, sequences of sucE1 genes have already been determined, so the genes can be obtained using primers prepared based on the nucleotide sequences. For example, a region including sucE1 and its adjacent region including sucE1-regulatory region of *C. glutamicum* can be obtained by PCR (polymerase chain reaction; see White, T. J. et al., Trends Genet. 5, 185 (1989)) using primers shown in SEQ ID NOS: 13 and 14 and using chromosomal DNA of a coryneform bacterium as a template. A homologue of sucE1 of another microorganism may be obtained in the same way as above.

The nucleotide sequences of sucE1 genes are different based on kinds or strains of coryneform bacteria, and therefore a sucE1 gene to be used for obtaining a bacterium used in the method of the present invention is not limited to a gene having the sequence of nucleotide numbers 571 to 2187 of SEQ ID NO: 15 or the sequence of SEQ ID NO: 17 or 19 and may be a mutant or artificially-modified gene that encodes a protein having a sequence of SEQ ID NO: 16, 18, or 20 including substitution, deletion, insertion, addition, etc. of one or several amino acids at one or plural positions as long as the gene improves the succinic acid-producing ability of the bacterium when expression of the gene is enhanced in the bacterium. In the present invention, although depending on the conformational positions or kinds of amino acid residues in a protein, the term “one or several” specifically means 1 to 20, preferably 1 to 10, more preferably 1 to 5. Meanwhile, the above-mentioned amino acid substitution, deletion, insertion, addition, inversion, or the like may be caused by a naturally-occurring mutation (mutant or variant) due to individual difference between bacteria having a sucE1 gene or difference in species of bacteria.

The above-mentioned substitution is preferably conservative substitution that is a neutral mutation causing no change in the functions. Examples of the conservative mutation include: when an aromatic amino acid is on a substitutional site, substitution among phe, trp, and tyr; when a hydrophobic amino acid is on a substitutional site, substitution among leu, ile, and val; in the case of a polar amino acid, substitution between gin and asn; in the case of a basic amino acid, substitution among lys, arg, and his; in the case of an acidic amino acid, substitution between asp and glu; and in the case of an amino acid having a hydroxyl group, substitution between ser and thr. Specific examples of the conservative substitution include: substitution of ser or thr for ala; substitution of gin, his, or lys for arg; substitution of glu, gln, lys, his, or asp for asn; substitution of asn, glu, or gln for asp; substitution of ser or ala for cys; substitution of asn, glu, lys, his, asp, or arg for gln; substitution of gly, asn, gln, lys, or asp for glu; substitution of pro for gly; substitution of asn, lys, gln, arg, or tyr for his; substitution of leu, met, val, or phe for ile; substitution of ile, met, val, or phe for leu; substitution of asn, glu, gln, his, or arg for lys; substitution of ile, leu, val, or phe for met; substitution of trp, tyr, met, ile, or leu for phe; substitution of thr or ala for ser; substitution of ser or ala for thr; substitution of phe or tyr for trp; substitution of his, phe, or trp for tyr; and substitution of met, ile, or leu for val.

Further, the sucE1 gene may have a sequence encoding a protein having homology of not less than 80%, preferably not less than 90%, more preferably not less than 95%, particularly preferably not less than 97%, to the whole amino acid sequence of SEQ ID NOS: 16, 18, or 20 and encoding a protein capable of improving succinic acid-producing ability of a bacterium when its expression is enhanced. Further, the degree of degeneracy of a gene varies depending on hosts where the gene is introduced, and therefore a codon may be substituted so that it is suitable for introduction of sucE1 into a host. Moreover, the sucE1 gene may be a gene encoding a protein with elongated or deleted sequence on the N- or C-terminal side as long as the gene has a function to improve the succinic acid-producing ability of a bacterium when its expression is enhanced. For example, the length of amino acid residue to be elongated or deleted is 50 or less, preferably 20 or less, more preferably 10 or less, particularly preferably 5 or less. More specifically, the sucE1 gene may be a gene encoding a protein having the amino acid sequence of SEQ ID NO: 16, 18, or 20 with elongation or deletion of five to 50 amino acids on the N-terminal side or five to 50 amino acids on the C-terminal side.

Genes homologous to the sucE1 gene can be obtained by modifying the nucleotide sequence of nucleotide numbers 571 to 2187 of SEQ ID NO: 15, or the nucleotide sequence of SEQ ID NO: 17 or 19 so that amino acid residues on a specific site of a protein encoded by the gene are substituted, deleted, inserted, or added, by, for example, the site-specific mutation. Meanwhile, the genes can be obtained by known mutation treatment as described below. The mutation treatment may be performed as follows: a mutation is artificially introduced into sucE1 by gene recombination by: treating in vitro the nucleotide sequence of nucleotide numbers 571 to 2187 of SEQ ID NO: 15, or the nucleotide sequence of SEQ ID NO: 17 or 19 with hydroxylamine or the like; treating a microorganism having the gene such as a coryneform bacterium by ultraviolet ray or by a mutagen to be used for a general mutation treatment such as N-methyl-N'-nitro-N-nitrosoguanidine (NTG) or ethylmethanesulfonate (EMS); error-prone PCR; DNA shuffling; or StEP-PCR, to introduce a mutation into a sucE1 gene artificially by gene recombination to yield a sucE1 gene with high activity (Firth A E, Patrick W M; Bioinformatics. 2005 Jun. 2; Statistics of protein library construction).

Whether or not such sucE1 homologous genes encode a protein capable of improving the succinic acid-producing ability by enhancing the expression can be confirmed by, for example, introducing these genes into a wild-type coryneform bacterium and examining the improvement of the succinic acid-producing ability.

Meanwhile, examples of the sucE1 gene include a DNA encoding a protein that hybridizes with a sequence complementary to the sequence of nucleotide numbers 571 to 2187 of SEQ ID NO: 15 or the nucleotide sequence of SEQ ID NO: 17 or 19, or a probe that is prepared from the sequences under stringent conditions and improves the succinic acid-producing ability of a bacterium when its expression is enhanced. The term “stringent conditions” as used herein refers to conditions where so-called specific hybrid is formed and non-specific hybrid is not formed. Examples thereof include: conditions where DNAs with high homology, for example, DNAs with at least 80% homology, preferably at least 90% homology, more preferably at least 95% homology, particularly preferably at least 97% homology hybridize with each other and DNAs with homology less than 80% do not hybridize with each other; or conditions for washing in general Southern hybridization, i.e., conditions comprising washing at temperature and salt concentration of 60° C., 1×SSC, 0.1% SDS, preferably 0.1×SSC, 0.1% SDS, more preferably 68° C., 0.1×SSC, 0.1% SDS once, more preferably two, or three times.

A partial sequence of the sequence of nucleotide numbers 571 to 2187 of SEQ ID NO: 15 or the sequence of SEQ ID NO: 17 or 19 may be used as a probe. Such a probe may be prepared by PCR using oligonucleotides prepared based on these nucleotide sequences as primers and using a DNA fragment containing the sequence as a template. For example, in the case of using a DNA fragment with a length of about 300 bp as a probe, a condition for washing in hybridization may be 50° C., 2×SSC, 0.1% SDS.

A bacterium is modified so that the expression level of the sucE1 gene described above is enhanced.

The phrase “modified so that expression of a sucE1 gene is enhanced” as used herein refers to a case where the number of SucE1 product molecules per cell is increased as compared to a parent strain or a wild-type strain, a case where the activity per SucE1 product molecule is enhanced, etc. Examples of the wild-type coryneform bacterium to be used for comparison include *Corynebacterium glutamicum* (*Brevibacterium lactofermentum*) ATCC 13869 or ATCC 13032.

The increased expression level of the sucE1 gene may be confirmed by comparing the m-RNA level of sucE1 with that of a wild-type or unmodified strain. Examples of methods of confirming the expression level include Northern hybridization and RT-PCR (Molecular cloning (Cold spring Harbor Laboratory Press, Cold spring Harbor (USA), 2001). The expression level may be any level as long as the level is increased as compared to a wild-type or unmodified strain, and for example, the level is desirably increased not less than 1.5-fold, more preferably not less than 2-fold, and further preferably not less than 3-fold as compared to a wild-type or unmodified strain.

The expression level of a sucE1 gene may be enhanced by increasing the copy number of the sucE1 gene. For example, the copy number of the sucE1 gene may be increased by: ligating a fragment containing a sucE1 gene to a vector that functions in a coryneform bacterium, preferably a multi-copy vector, to prepare a recombinant DNA; and introducing the DNA into a coryneform bacterium having succinic acid-producing ability as described above to transform the cells. Alternatively, the copy number of the sucE1 gene may be increased by: introducing the above-mentioned recombinant DNA into a wild-type coryneform bacterium to yield a transformed strain; and imparting the succinic acid-producing ability to the transformed strain. Meanwhile, the copy number can be increased by transferring one copy or multiple copies of a gene encoding sucE1 on a chromosome. The transfer of the sucE1 gene on a chromosome can be confirmed by Southern hybridization using a part of the sucE1 gene as a probe.

Meanwhile, the expression of a sucE1 gene can be enhanced by modifying an expression regulatory sequence of the sucE1 gene. For example, the enhancement can be achieved by replacing a promoter sequence of sucE1 with a stronger promoter or by making a promoter sequence close to a consensus sequence (WO 00/18935).

Methods of constructing a microorganism having succinic acid-producing and modified so that the expression level of a sucE1 gene is increased are shown below. These methods can be performed in accordance with a manual such as Molecular cloning (Cold spring Harbor Laboratory Press, Cold spring Harbor (USA), 2001).

The expression level of the gene can be enhanced by increasing the copy number of a sucE1 gene, and the copy number can be increased by amplifying the sucE1 gene with a plasmid as described below. First, a sucE1 gene is cloned from a chromosome of a coryneform bacterium or the like. A chromosomal DNA can be prepared from a bacterium serving as a DNA donor by, for example, the method of Saito and Miura (see H. Saito and K. Miura, Biochem. Biophys. Acta, 72, 619 (1963), Experiment Manual for Biotechnology, edited by The Society for Biotechnology, Japan, p 97-98, Baifukan Co., Ltd., 1992) or the like. Oligonucleotides to be used in PCR can be synthesized based on the above-mentioned known information, and for example, the synthetic oligonucleotides described in SEQ ID NOS 13 and 14 may be used to amplify a sucE1 gene.

A gene fragment comprising a sucE1 gene amplified by PCR is preferably amplified by inserting the fragment into a vector having a replication origin that is autonomously replicable in a microorganism and the vector is used to transform a bacterium. In particular, in the case of introducing the fragment into a coryneform bacterium, if a recombinant DNA prepared by connecting the fragment to a vector DNA that is autonomously replicable in cells of *Escherichia coli* and/or a coryneform bacterium is introduced into *Escherichia coli*, subsequent operations are easily performed. Examples of the vector that is autonomously replicable in cells of *Escherichia coli* include pUC19, pUC18, pHSG299, pHSG399, pHSG398, RSF1010, pBR322, pACYC184, and pMW219.

In the case of using a coryneform bacterium as a host, the above-mentioned DNA may be inserted into a vector that functions in coryneform bacteria. The vector that functions in coryneform bacteria is, for example, a plasmid that is able to autonomously replicable in coryneform bacteria. Specific examples of the plasmid that is autonomously replicable in coryneform bacteria include: plasmid pCRY30 described in JP 03-210184 A; plasmids pCRY21, pCRY2KE, pCRY2KX, pCRY31, pCRY3KE, and pCRY3KX described in JP 02-72876 A and U.S. Pat. No. 5,185,262; plasmids pCRY2 and pCRY3 described in JP 01-191686 A; pAM330 described in JP 58-67679 A; pHM1519 described in JP 58-77895 A; pAJ655, pAJ611, and pAJ1844 described in JP 58-192900 A; pCG1 described in JP 57-134500 A; pCG2 described in JP 58-35197 A; pCG4, pCG11, etc. described in JP 57-183799 A; and pVK7 described in JP 10-215883 A.

Further, a vector obtained by excising a DNA fragment which enables a plasmid to autonomously replicate in coryneform bacteria from any of those vectors and inserting the fragment into the vector for *Escherichia coli* can be used as a so-called shuttle vector which is autonomously replicable both in *Escherichia coli* and coryneform bacteria.

To prepare a recombinant DNA by ligation of a sucE1 gene to a vector that functions in coryneform bacteria, the vector is cleaved with a restriction enzyme suitable for the end of sucE1. The restriction enzyme site may be introduced in advance into a synthetic oligonucleotide to be used for amplifying sucE1. Ligation is usually performed using a ligase such as T4 DNA ligase.

In order to introduce a recombinant plasmid prepared as described above into a bacterium, any known transformation method reported so far can be employed. For example, treating recipient cells with calcium chloride so as to increase the permeability of DNA, which has been reported for *Escherichia coli* K-12 (Mandel, M. and Higa, A., J. Mol. Biol., 53, 159 (1970)), and using competent cells prepared from growing cells to introduce a DNA, which has been reported for *Bacillus subtilis* (Duncan, C. H., Wilson, G. A. and Young, F. E., Gene, 1, 153 (1977)) can be employed. In addition to these methods, introducing a recombinant DNA into protoplast- or spheroplast-like DNA recipient cells where a recombinant DNA can be easily integrated, which have been reported to be applicable to *Bacillus subtilis*, actinomycetes, and yeasts (Chang, S. and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)), can be employed. In addition, transformation of bacteria can also be performed by the electric pulse method (JP 02-207791 A) or by the conjugal transfer method (Biotechnology (NY). 1991 January; 9(1): 84-7).

The copy number of sucE1 can be increased by integrating multiple copies of sucE1 into a chromosomal DNA of a bacterium. In order to integrate multiple copies of sucE1 into a chromosomal DNA of a bacterium, homologous recombination may be performed by targeting a sequence which exists in multiple copies on a chromosomal DNA. The sequence which exists in multiple copies on a chromosomal DNA may be a repetitive DNA or inverted repeat at an end of a transposon. Alternatively, as disclosed in JP 02-109985 A, the copy number can be increased by carrying sucE1 on a transposon and transferring it to integrate multiple copies of the gene into a chromosomal DNA (JP 02-109985 A, JP 07-107976 A, Mol. Gen. Genet., 245, 397-405 (1994), Plasmid. 2000 November; 44(3): 285-91).

Also, the copy number of sucE1 can be increased by: introducing a sucE1 gene into a plasmid having a replication origin that cannot be replicated in a host or a plasmid having a replication origin that cannot replicate in a host and a conjugal transfer ability to a host; and amplifying the gene on chromosome. Examples of a vector to be used include pSUP301 (Simo et al., Bio/Technology 1, 784-791 (1983)), pK18mob or pK19mob (Schaefer et al., Gene 145, 69-73 (1994)), pGEM-T (Promega corporation, Madison, Wis., USA), pCR2.1-TOPO (Shuman (1994). Journal of Biological Chemistry 269: 32678-84; U.S. Pat. No. 5,487,993), PCR$^{(R)}$ Blunt (Invitrogen, Groningen, Netherlands; Bernard et al., Journal of Molecular Biology, 234: 534-541 (1993)), pEM1 (Schrumpf et al., 1991, Journal of Bacteriology 173: 4510-4516), and pBGS8 (spratt et al., 1986, Gene, 41:337-342). A plasmid vector comprising a sucE1 gene is transferred into a bacterium by conjugation or transformation. A conjugation method is described by, for example, Schaefer et al. (Applied and Environmental Microbiology 60, 756-759 (1994)). A transformation method is described by, for example, Theirbach et al. (Applied Microbiology and Biotechnology 29, 356-362 (1988)), Dunican and Shivinan (Bio/Technology 7, 1067-1070 (1989)), and Tauch et al. (FEMS Microbiological Letters 123, 343-347 (1994)).

Meanwhile, the activity of sucE1 may be increased by: substituting an expression regulatory sequence such as a promoter of sucE1 on a chromosomal DNA or on a plasmid with a stronger promoter; modifying a factor involved in the regulation of sucE1 expression, for example, an operator or a repressor; or ligating a stronger terminator (Hamilton et al.,; Journal of Bacterology 171: 4617-4622). Examples of known strong promoters include lac promoter, trp promoter, trc promoter, and PS2 promoter. Examples of a method of evaluating promoter strength and strong promoters are described by Goldstein et al. (Prokaryotic promoters in biotechnology. Biotechnol. Annu. Rev., 1995, 1. 105-128). As disclosed in WO 00/18935, a promoter may be modified into a stronger one by introducing a nucleotide substitution of several nucleotides in a promoter region of a target gene so that the sequence is closer to a consensus sequence. For example, the −35 region may be changed to TTGACA or TTGCCA, while the −10 region may be changed to TATAAT and TATAAC. In addition, it is known that translation efficiency of mRNA is significantly affected by a substitution of several nucleotides in a sequence of a spacer between a ribosome binding site (RBS) and a translation initiation codon, in particular, a sequence immediately upstream of the initiation codon, and the sequence may be modified.

Expression level may be increased by extending the survival time of m-RNA or by preventing degradation of an enzyme protein in a cell. An expression regulatory sequence such as a promoter at the upstream of a sucE1 gene can be identified using a promoter search vector or gene-finding software such as GENETYX. Such promoter substitution or modification enhances the expression of a sucE1 gene. Substitution of an expression regulatory sequence may be performed using a temperature-sensitive plasmid, for example. Examples of a temperature-sensitive plasmid of a coryneform bacterium include p48K, pSFKT2 (JP 2000-262288 A), and pHSC4 (FR 1992-2667875 A and JP 05-7491 A). These plasmids are autonomously replicable at least at 25° C. but are not autonomously replicable at 37° C. *Escherichia coli* AJ12571 carrying pHSC4 was deposited in the National Institute of Bioscience and Human-Technology, Agency of Industrial Science and Technology (currently, International Patent Organism Depositary, National Institute of Advanced Industrial Science and Technology, Central 6, 1-1-1 Higashi, Tsukuba, Ibaraki 305-8566, Japan) on Oct. 11, 1990 and given an accession number of FERM P-11763, and the deposit was then converted to an international deposit under the provisions of Budapest Treaty on Aug. 26, 1991 and given an accession number of FERM BP-3524.

Modification of an expression regulatory sequence may be combined with enhancement of the copy number of a sucE1 gene.

In the method of the present invention, it is more effective to use a bacterial strain modified so that, in addition to an increase in the expression of sucE, the lactate dehydrogenase (LDH) activity is decreased. The phrase "lactate dehydrogenase activity is decreased" as used herein refers to a decrease in the lactate dehydrogenase activity as compared to that of a lactate dehydrogenase-unmodified strain. The lactate dehydrogenase activity is preferably decreased to 10% or less per bacterial cell as compared to that of a lactate dehydrogenase-unmodified strain. In addition, the lactate dehydrogenase activity may be completely lost. The decrease in the lactate dehydrogenase activity can be confirmed by measuring a lactate dehydrogenase activity by a known method (L. Kanarek and R. L. Hill, J. Biol. Chem. 239, 4202 (1964)). Specific examples of a method of producing a mutant obtained by modifying a coryneform bacterium so that the lactate dehydrogenase activity is decreased include homologous recombination into chromosomes described in JP 11-206385 A and a method using a SacB gene described in Examples in the present description (Schafer, A. et al. Gene 145 (1994) 69-73). A coryneform bacterium of the present invention, modified so that the expression of sucE1 is enhanced and the lactate dehydrogenase activity is decreased, may be obtained by: preparing a bacterium in which an LDH gene has been disrupted by, for example, the method described in Example 2 below; and transforming the bacterium with a recombinant vector comprising a sucE1 gene. However, there is no preference between the modification for decreasing the LDH activity and the expression of a sucE1 gene.

In order to decrease or eliminate the LDH activity, a mutation to achieve a decrease or loss in the LDH activity in a cell may be introduced into an LDH gene on a chromosome by a general mutation treatment method. For example, it may be achieved by deleting a gene encoding LDH on a chromosome by gene recombination or by modifying an expression regulatory sequence such as a promoter or Shine-Dalgarno (SD) sequence. In addition, it may be achieved by: introducing an amino acid substitution (missense mutation) in regions encoding LDH on a chromosome; introducing a stop codon (nonsense mutation); introducing a frameshift mutation that adds or deletes one or two nucleotides; or deleting a partial or entire region of a gene (Journal of Biological Chemistry 272: 8611-8617 (1997). Meanwhile, a decrease or loss in the LDH activity may be achieved by constructing a gene encoding a mutant LDH with a deletion in a coding region and replacing a normal LDH gene on a chromosome with the gene by homologous recombination or introducing a transposon or an IS factor into the gene.

In order to introduce a mutation to decrease or eliminate the LDH activity by gene recombination, the following method may be used, for example. An LDH gene on a chromosome may be replaced with the mutant LDH gene by: preparing a mutant LDH gene by modifying a partial sequence of an LDH gene so that an enzyme capable of functioning normally is not produced; transforming a coryneform bacterium with a DNA comprising the gene; and performing a recombination between the mutant gene and a gene on a chromosome. Such site-specific mutation by gene substitution using homologous recombination has been established and can be achieved by a method using a linear DNA or a method using a plasmid containing a temperature-sensitive replication origin (U.S. Pat. No. 6,303,383 or JP 05-007491 A). Meanwhile, the site-specific mutation by gene substitution using homologous recombination may be performed by using a plasmid having no replication ability in a host. Examples of a temperature-sensitive plasmid of a coryneform bacterium include the above-mentioned p48K, pSFKT2 (U.S. Pat. No. 6,303,383), and pHSC4 (FR 1992-2667875 A and JP 05-7491 A).

In addition, in a process for disrupting a gene as described above, levansucrase may be used as a marker for gene recombination (Schafer, A. et al. Gene 145 (1994) 69-73).

In the reaction of the present invention, a bacterium modified so that, in addition to the enhancement of the expression of sucE1, the pyruvate carboxylase activity is enhanced. The phrase "the pyruvate carboxylase activity is enhanced" refers to an increase in the pyruvate carboxylase activity as compared to that of an unmodified strain such as a wild-type or parent strain. The pyruvate carboxylase activity can be measured by, for example, a method of measuring a reduction in NADH as described below. A coryneform bacterium modified so that expressions of sucE1 and pyruvate carboxylase are enhanced can be prepared by expressing the sucE1 gene and pyruvate carboxylase (PC) gene at high levels in a coryneform bacterium in the same way as the method described in JP 11-196888 A.

A PC gene to be used in a method of the present invention is a gene having a determined nucleotide sequence or a gene obtained by isolating a DNA fragment encoding a protein having PC activity from a chromosome of any of microorganisms, animals, plants, etc. and determining the nucleotide sequence. After the determination of the nucleotide sequence, a gene synthesized based on the sequence may be used.

Examples of the PC gene include a PC gene derived from a coryneform bacterium such as *Corynebacterium glutamicum* (Peters-Wendisch, P. G. et al. Microbiology, vol. 144 (1998) p 915-927) (SEQ ID NO: 21). Further, for the PC gene, as long as there is no substantial defect in functions of encoded PC, i.e., the properties involved in carbon dioxide fixation, part of nucleotides in the nucleotide sequence of SEQ ID NO. 21 may be substituted with other nucleotides, deleted, or inserted with another nucleotide. Alternatively, part of the nucleotide sequence may be dislocated. Any of these derivatives can be used in the present invention. A DNA that hybridizes with a DNA having a nucleotide sequence of SEQ ID NO: 21 under stringent condition, or a DNA that has homology of not less than 90%, preferably not less than 95%, or more preferably not less than 99% to the nucleotide sequence of SEQ ID NO: 21, and encodes a protein having the PC activity, can be preferably used. Here, the stringent condition includes any of conditions that allow hybridization at salt concentrations corresponding to washing conditions in the conventional southern hybridization, 60° C., 1×SSC, 0.1% SDS, and preferably 0.1×SSC, 0.1% SDS.

The PC gene obtained from any of bacteria other than *Corynebacterium glutamicum*, or from any of microorganisms, animals, and plants can be also used. In particular, the PC genes from the microorganisms, animals, and plants, such as those described below, have known sequences (references are indicated below). The PC gene can be obtained by the same way as described above with hybridization or the amplification of ORF portions with the PCR method.

*Homo sapiens* [Biochem. Biophys. Res. Comm., 202, 1009-1014, (1994)]

*Mus musculus* [Proc. Natl. Acad. Sci. USA., 90, 1766-1779, (1993)]

Rat [GENE, 165, 331-332, (1995)]

Yeast; *Saccharomyces cerevisiae* [Mol. Gen. Genet., 229, 307-315, (1991)]

*Schizosaccharomyces pombe* [DDBJ Accession No.; D78170]

*Bacillus stearothermophilus* [GENE, 191, 47-50, (1997)]

*Rhizobium etli* [J. Bacteriol., 178, 5960-5970, (1996)]

The enhancement of a PC gene can be performed in the same way as that in the case of a sucE1 gene as described above.

In the present invention, succinic acid is produced using a bacterium having succinic acid-producing ability and modified so that expression of a sucE1 gene is enhanced.

Upon using the above-mentioned bacterium in the reaction for production of succinic acid, cells subjected to slant culture on a solid medium such as an agar medium may be used, and preferably the above-mentioned bacterium may be cultured in advance in a liquid medium (seed culture) before use. Succinic acid is produced by allowing such a seed-cultured bacterium to act on organic raw material while the bacterium is growing in a medium containing carbonate ion, bicarbonate ion, or carbon dioxide, and organic materials. In the case of using an aerobic coryneform bacterium for the process of the present invention, it is preferable to use the bacterium after incubating the bacterial cells under normal aerobic condition. The medium used for the incubation may be any medium normally used for the cultivation of microorganisms. For instance, a conventional medium, which is prepared by adding a natural nutrient source such as meat extract, yeast extract, or peptone to a composition containing inorganic salt such as ammonium sulfate, potassium phosphate, or magnesium sulfate, can be used. The bacterial cells after culturing are harvested by centrifugation, membrane separation, or the like and then used for the reaction.

In the present invention, treated cells of bacterial cells can be also used. For instance, the treated cells of bacterial cells include immobilized bacterial cells being immobilized on acrylamide, carrageenan, or the like, debris of crushed bacterial cells, centrifugal supernatant thereof, or fraction obtained by partially purifying the supernatant with ammonium sulfate treatment or the like.

An organic raw material to be used in the method of the present invention is not limited as long as the material is a carbon source which can be assimilated by the microorganism of the present invention and converted to succinic acid. Generally, a fermentable carbohydrate of: carbohydrate such as galactose, lactose, glucose, fructose, glycerol, sucrose, saccharose, starch, or cellulose; or polyalcohol such as glycerin, mannitol, xylitol, or ribitol may be used. Of these, glucose, fructose, and glycerol are preferable, and glucose is particularly preferable.

In addition, a starch saccharification liquid, molasses, or the like, which contains the above fermentable carbonhydrates, can be also used. These fermentable carbonhydrates may be used solely or in combination. The amount of the above organic raw material is not specifically limited and it is advantageous to increase as much as possible within the range that does not inhibit the generation of succinic acid, generally in the range of 5 to 30% (w/v), preferably 10 to 20% (w/v). Further, the organic raw materials may be supplementary added in conformity to a decrease in the above organic raw material due to the progress of the reaction.

The reaction liquid containing the carbonate ion, the bicarbonate ion, or carbon dioxide, and the organic raw materials is not specifically limited and, for instance, may be any of culture media for culturing bacteria or any of buffers including a phosphate buffer. The reaction liquid is preferably an aqueous solution containing a nitrogen source, an inorganic salt, and the like. Here, the nitrogen source is not specifically limited as long as it can generate succinic acid by assimilation of the microorganism of the present invention. Specifically, the nitrogen sources include various organic and inorganic nitrogen compounds such as ammonium salt, nitrate, urea, soybean hydrolysate, casein hydrolysate, peptone, yeast extract, meat extract, and corn steep liquor. The inorganic salts include various kinds of phosphate, sulfate, and metal salts of magnesium, potassium, manganese, iron, zinc, and the like. In addition, any of factors that promote the growth of bacterial cells, including vitamins such as biotin, pantothenic acid, inositol, and nicotinic acid, nucleotides, and amino acids, may be added if necessary. Further, it is desirable that an optimum amount of a commercial antifoaming agent is added to the medium to suppress foaming at the time of reaction.

The pH of the reaction liquid can be adjusted by the addition of sodium carbonate, sodium bicarbonate, potassium carbonate, potassium bicarbonate, magnesium carbonate, sodium hydroxide, calcium hydroxide, magnesium hydroxide, or the like. The pH for the reaction of the present invention is usually pH of 5 to 10, preferably pH of 6 to 9.5, so the pH of the reaction liquid can be adjusted within the above range with an alkaline material, carbonate, urea, or the like even during the reaction if required.

The reaction liquid used in the present invention may be water, a buffer, a medium, or the like, but the medium is preferable. The medium may contain, for instance, the organic raw materials described above together with carbonate or bicarbonate ion, or carbon dioxide and the reaction may be carried out under anaerobic conditions. The carbonate ion or bicarbonate ion may be supplied from magnesium carbonate, sodium carbonate, sodium bicarbonate, potassium carbonate, or potassium bicarbonic acid, which can be also used as a neutralizing agent. However, if required, the carbonate ion or bicarbonate ion can be also supplied from carbonic acid or bicarbonic acid or salts thereof or carbon dioxide. The specific examples of the salts of carbonic acid or bicarbonate include magnesium carbonate, ammonium carbonate, sodium carbonate, potassium carbonate, ammonium bicarbonate, sodium bicarbonate, and potassium bicarbonate. In addition, the carbonate ion or bicarbonate ion is added at a concentration of 0.001 to 5 M, preferably 0.1 to 3 M, more preferably 1 to 2 M. When the carbon dioxide is contained, the amount of carbon dioxide contained is 50 mg to 25 g, preferably 100 mg to 15 g, more preferably 150 mg to 10 g per litter of the solution.

The optimal temperature for bacterial growth to be used in the reaction of the present invention is generally in the range of 25 to 35° C. The temperature of the reaction is generally in the range of 25 to 40° C., preferably in the range of 30 to 37° C. The number of bacterial cells used in the reaction is, but not specifically limited to, 1 to 700 g/L, preferably 10 to 500 g/L, more preferably 20 to 400 g/L. The reaction time is preferably 1 to 168 hours, more preferably 3 to 72 hours.

For culturing the bacterium, it is necessary to supply oxygen by aeration and agitation. On the other hand, succinic acid may be produced in the reaction with aeration and agitation or may be produced in the reaction under anaerobic conditions with neither aeration nor supply of oxygen. Here, the term "anaerobic conditions" used herein means that a reaction is conducted while keeping the dissolved oxygen concentration low in solution. In this case, it is preferable to carry out a reaction at a dissolved oxygen concentration of 0 to 2 ppm, preferably 0 to 1 ppm, more preferably 0 to 0.5 ppm. For that purpose, a method may be: a method in which a vessel is hermetically sealed to carry out the reaction under no aerating condition; a method in which inert gas such as nitrogen gas is supplied and reacted; or a method in which aeration with inert gas containing carbon dioxide is performed.

Succinic acid accumulated in the reaction liquid (culture solution) can be isolated and purified from the reaction liquid according to the conventional procedures. Specifically, succinic acid can be isolated and purified by removing solid components of bacterial cells or the like by centrifugation, filtration, or the like, and desalting with an ion exchange resin or the like, followed by crystallization from the solution, or column chromatography.

Further, in the present invention, after the production of succinic acid by the method of the present invention as described above, a polymerization reaction may be carried out using the obtained succinic acid as a raw material to produce a succinic acid-containing polymer. In recent years, while the number of environment-friendly industrial products is on the increase, polymers prepared by using raw materials of a plant origin have been attracting attention. The succinic acid to be produced in the present invention can be processed into polymers such as polyester and polyamide. Specific examples of the succinic acid-containing polymer include a succinic acid polyester obtained through polymerization between a diol such as butanediol or ethylene glycol and succinic acid, and a succinic acid polyamide obtained through polymerization between a diamine such as hexamethylenediamine and succinic acid. In addition, the succinic acid or a composition containing the succinic acid that can be obtained by the method of the present invention can be used for food additives, pharmaceuticals, cosmetics, and the like.

Example 1

Construction of a Vector for Gene Disruption (A) Construction of pBS3

The plasmid pBS3 was obtained by PCR using the chromosomal DNA of *Bacillus subtilis* as a template while using SEQ ID NOS: 1 and 2 as primers. The PCR reaction was carried out using LA taq (TaKaRa) such that one cycle of heat-retention at 94° C. for 5 minutes was performed and then a cycle of denaturation at 94° C. for 30 seconds, annealing at 49° C. for 30 seconds, and elongation at 72° C. for 2 minutes was repeated 25 times. The PCR product thus obtained was purified by the conventional procedures and then digested with BglII and BamHI, followed by blunt-ending.

The fragment was inserted into the site pHSG299 digested with AvaII and blunt-ended. The DNA was used to transform competent cells of *Escherichia coli* JM109 (TAKARA SHUZO CO., LTD.) and transformed cells were applied on an LB medium containing 25 μg/ml kanamycin (hereinafter, abbreviated as Km), followed by overnight culture. Subsequently, appeared colonies were picked up, and a single colony was then isolated, thereby a transformant was obtained. A plasmid was extracted from the resultant transformant, and a plasmid into which the PCR product of interest was inserted, was named pBS3. FIG. 1 shows the construction procedure of pBS3.

(B) Construction of pBS4S

A plasmid in which SmaI site of a Km resistance gene present on pBS3 is disrupted by nucleotide substitution causing no amino acid substitution was obtained by crossover PCR. First, PCR was carried out using pBS3 as a template and using synthetic DNAs of SEQ ID NOS: 3 and 4 of the Sequence Listing as primers, to obtain an amplified product of the N-terminal region of the Km resistance gene. On the other hand, to obtain an amplified product of the C-terminal region of the Km resistance gene, PCR was carried out using pBS3 as a template and using synthetic DNAs of SEQ ID NOS: 5 and 6 of the Sequence Listing as primers. The PCR was carried out using Pyrobest DNA Polymerase (TaKaRa) such that one cycle of heat-retention at 98° C. for 5 minutes was performed and then a cycle of denaturation at 98° C. for 10 seconds, annealing at 57° C. for 30 seconds, and elongation at 72° C. for 1 minute was repeated 25 times, to thereby yield the PCR product of interest.

Figure 2:
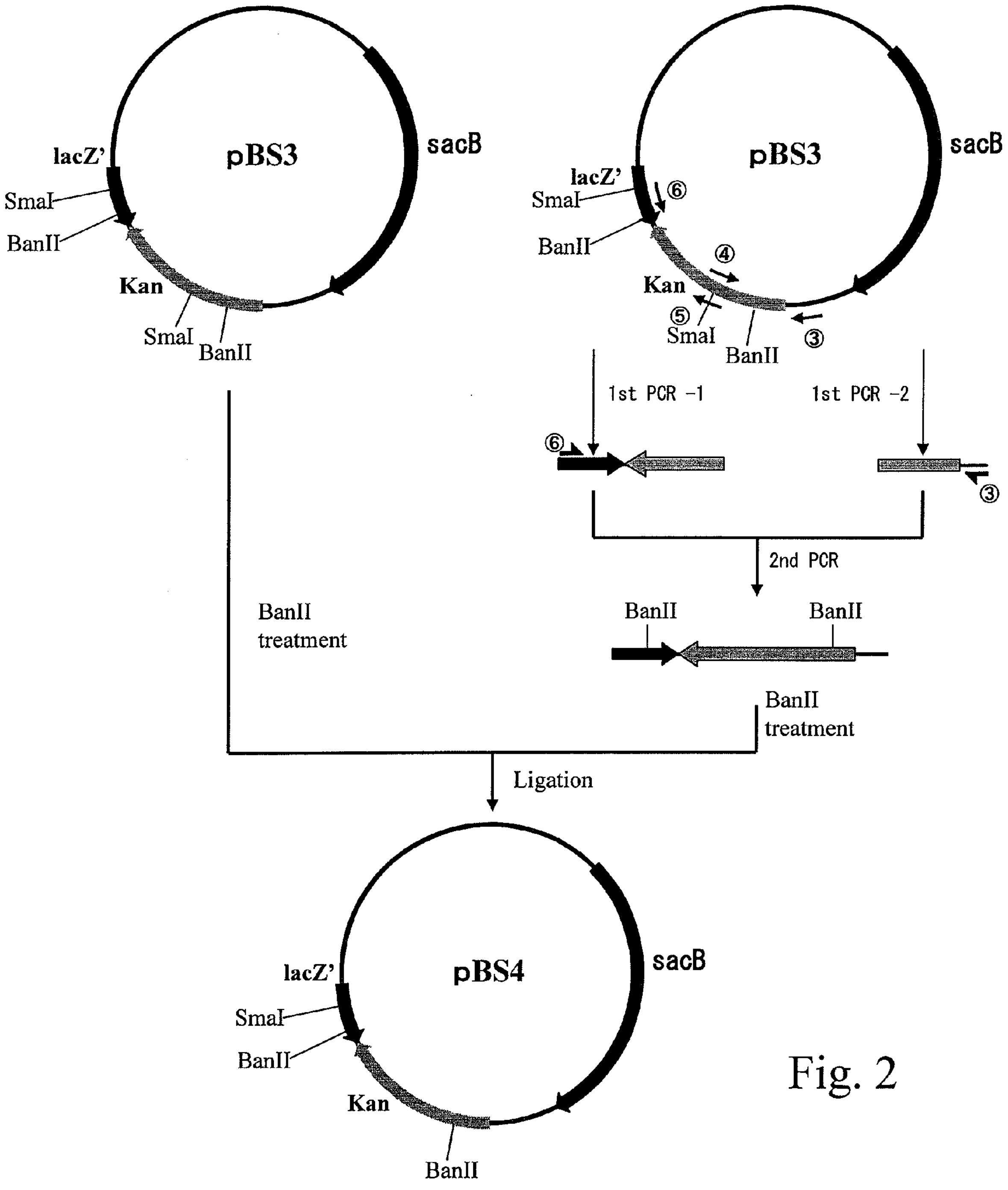
FIG. 2 A drawing showing the construction of the plasmid pBS4 for gene disruption. The numbers in the circles show the SEQ ID NOs of the primers.

SEQ ID NOS: 4 and 5 of the Sequence Listing are partially complementary with each other, and the SmaI site in the sequences was disrupted by nucleotide substitution causing no amino acid substitution. Next, to obtain a fragment of the mutant Km resistance gene containing the disrupted SmaI site, the gene products of the N-terminal and C-terminal regions of the above-mentioned Km resistance gene were mixed at an approximately equimolar concentration, and PCR was carried out using the mixture of the gene products as a template and synthetic DNAs of SEQ ID NOS: 3 and 6 of the Sequence Listing as primers, to thereby obtain an amplified product of a mutation-introduced Km resistance gene. PCR was carried out using Pyrobest DNA Polymerase (TaKaRa) such that one cycle of heat-retention at 98° C. for 5 minutes was performed and then a cycle of denaturation at 98° C. for 10 seconds, annealing at 57° C. for 30 seconds, and elongation at 72° C. for 1.5 minutes was repeated 25 times, to thereby obtain the PCR product of interest. The PCR product was purified by the conventional procedures and then digested with BanII, followed by insertion into the BanII site in the above-mentioned pBS3. The obtained DNA was used to transform competent cells of *Escherichia coli* JM109 (TAKARA SHUZO CO., LTD.) and transformed cells were applied on an LB medium containing 25 μg/ml of Km, followed by overnight culture. Subsequently, appeared colonies were picked up, and a single colony was isolated, thereby a transformant was obtained. Plasmid was extracted from the resultant transformant, and a plasmid into which the PCR product of interest was inserted was named pBS4S. FIG. 2 shows the construction process of pBS4S.

Example 2

Figure 3:
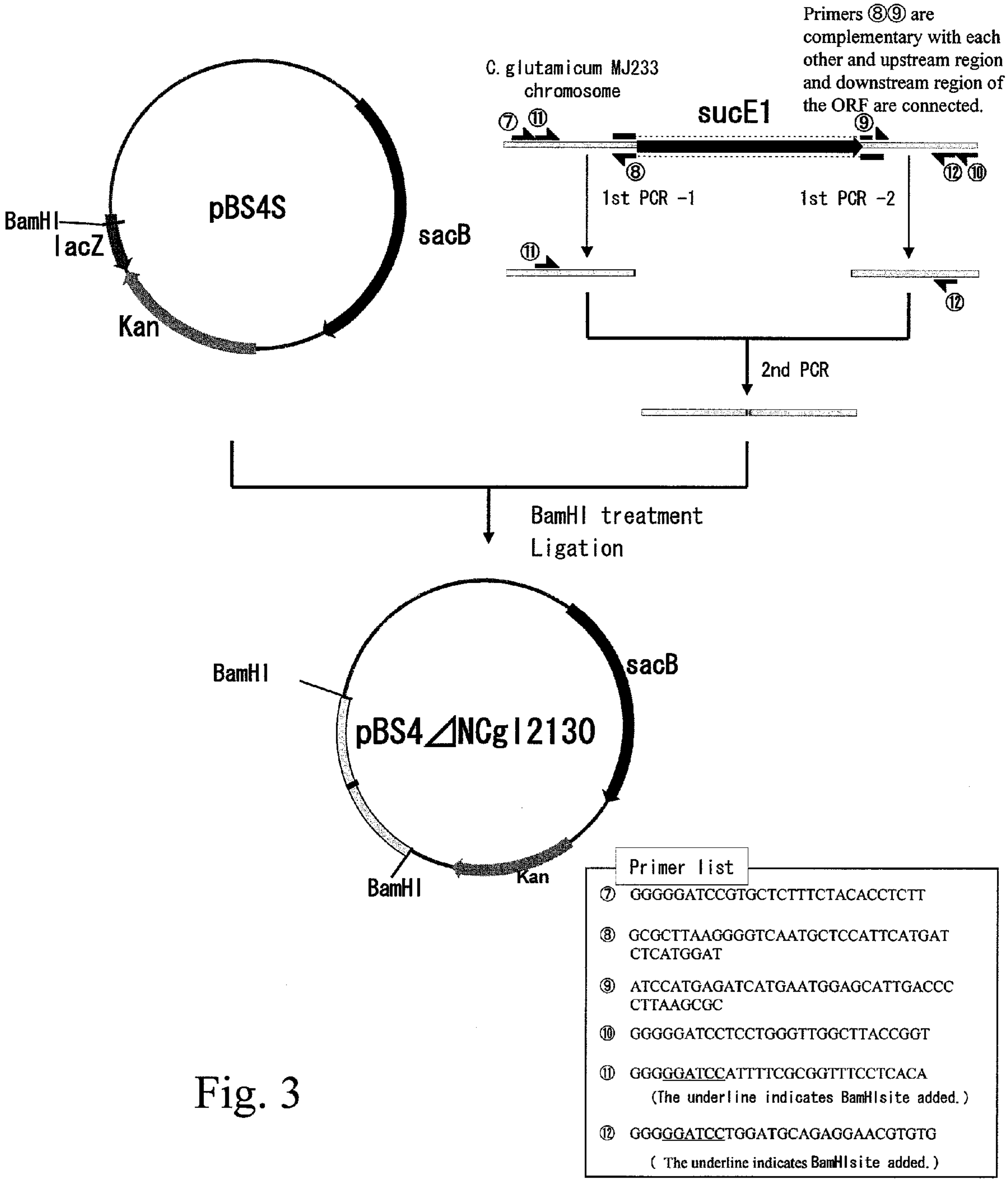
FIG. 3 A drawing showing the construction of a plasmid for disrupting sucE1. The numbers in the circles show the SEQ ID NOs of the primers.

Construction of a sucE1 Gene-Disrupted Strain (A) Cloning of a Fragment for Disrupting sucE1 Gene A fragment of a gene in which the ORF of sucE1 gene derived from *Brevibacterium flavum* MJ233 strain was deleted was obtained by crossover PCR using synthetic DNAs which were designed based on the nucleotide sequence around NCgl2130 of the gene of *Corynebacterium glutamicum* ATCC 13032 (GenBank Database Accession No. NC#003450), which has already been disclosed, as primers. Specifically, PCR was carried out by the conventional procedures using a chromosomal DNA of *Brevibacterium flavum* MJ233 strain as a template and using synthetic DNAs of SEQ ID NOS: 7 and 8 of the Sequence Listing as primers, to obtain an amplified product of the N-terminal region of the sucE1 gene. On the other hand, to obtain an amplified product of the C-terminal region of the sucE1 gene, PCR was carried out by the conventional procedures using a genomic DNA of *Brevibacterium flavum* MJ233 as a template and using synthetic DNAs of SEQ ID NOS: 9 and 10 of the Sequence Listing as primers. PCR was carried out using Pyrobest DNA Polymerase (TaKaRa) such that one cycle of heat-retention at 94° C. for 3 minutes was performed and then a cycle of denaturation at 94° C. for 30 seconds, annealing at 60° C. for 30 seconds, and elongation at 72° C. for 1 minute was repeated 30 times, to thereby yield the PCR product of interest. SEQ ID NOS: 8 and 9 of the Sequence Listing are complementary with each other and have structures in which the entire sequences of orf in sucE1 are deleted. Next, to obtain a fragment of the sucE1 gene in which an internal sequence is deleted, the gene products of the N-terminal and C-terminal regions in the above-mentioned sucE1 were mixed at an approximately equimolar concentration, and PCR was carried out by the conventional procedures using the mixture of the gene products as a template and using synthetic DNAs of SEQ ID NOS: 11 and 12 of the Sequence Listing as primers, to yield an amplified product of orf-deleted sucE1 gene. The PCR was carried out using Pyrobest DNA Polymerase (TaKaRa) such that one cycle of heat-retention at 94° C. for 3 minutes was performed and then a cycle of denaturation at 94° C. for 30 seconds, annealing at 58° C. for 30 seconds, and elongation at 72° C. for 2 minutes was repeated 30 times, to yield a PCR product of interest. The PCR product thus produced was purified by the conventional procedures and then digested with BamHI, followed by insertion into the BamH1 site of the pBS4S constructed in the item (B) of Example 1. The obtained DNA was used to transform competent cells of *Escherichia coli* JM109 (TAKARA SHUZO CO., LTD.) and the transformed cells were applied on an LB medium containing 100 μM of IPTG, 40 μg/ml of X-Gal, and 25 μg/ml of Km, followed by overnight culture. Subsequently, appeared white colonies were picked up, and then a single colony was isolated, thereby a transformant was obtained. Plasmid was extracted from the resultant transformant, a plasmid into which the PCR product of interest was inserted was named pBS4SΔsucE1. FIG. 3 shows the construction process of the plasmid.

(B) Preparation of sucE1-Disrupted Strain

The pBS4SΔsucE1 obtained in the above-mentioned item (A) does not contain a region that enables autonomous replication in a cell of a coryneform bacterium. Therefore, when a coryneform bacterium is transformed with the plasmid, a strain in which the plasmid is integrated into a chromosome by homologous recombination appears at a very low frequency as a transformant. *Brevibacterium flavum* MJ233ΔLDH strain (MJ233/ΔLDH strain described in JP 2005-95169 A) was transformed using a high concentration of the plasmid pBS4SΔsucE1 by the electrical pulse method, and the transformed cells were applied on CM-Dex agar medium (5 g/L glucose, 10 g/L polypeptone, 10 g/L yeast extract, 1 g/L $KH_2PO_4$, 0.4 g/L $MgSO_4.7H_2O$, 0.01 g/L $FeSO_4.7H_2O$, 0.01 g/L $MnSO_4.7H_2O$, 3 g/L urea, 1.2 g/L soybean hydrolysate, pH 7.5 (KOH), and supplemented with 1.5% agar) containing 50 μg/ml of kanamycin, followed by culture at 31.5° C. for about 24 hours. Note that the plasmid used was one extracted from a transformant of *Escherichia coli* SCS110 (Stratagene) transformed with pBS4SΔsucE1. In the case where homologous recombination occurred between the sucE1 gene fragment of the plasmid and the same gene on genome of *Brevibacterium flavum* MJ233 strain, the colonies grown on the medium must have a kanamycin resistant gene and a SacB gene derived from the plasmid on the same genome.

Subsequently, the single cross over recombinants were cultured in a CM-Dex liquid medium containing no kanamycin at 31.5° C. overnight and, after suitable dilution, applied on Dex-S10 agar medium containing 10% sucrose and no kanamycin (100 g/L sucrose, 10 g/L polypeptone, 10 g/L yeast extract, 1 g/L $KH_2PO_4$, 0.4 g/L $MgSO_4.7H_2O$, 0.01 g/L $FeSO_4.7H_2O$, 0.01 g/L $MnSO_4.4H_2O$, 3 g/L urea, 1.2 g/L soybean hydrolysate, 10 μg/L biotin, pH 7.5 (KOH), and supplemented with 1.5% agar) and cultured at 31.5° C. for about 24 hours, to thereby yield sucrose-resistant clones. The strains were modified so as not to express a normal sacB gene and include strains from which pBS4SΔsucE1 was cured by the second homologous recombination. Further, the strains subjected to the second homologous recombination include a strain where a sucE1 gene was replaced by a deleted-type gene derived from pBS4SΔsucE1 and a strain where a sucE1 gene reverted to a wild-type gene. Whether the sucE1 gene is a mutant type or a wild type can be confirmed easily by: extracting chromosomal DNAs from bacterial cells obtained by culture in a Dex-S10 agar medium; and detecting a sucE1 gene by PCR. Among the resultant second cross over recombinants, a strain of a PCR product having a size smaller than that obtained by PCR using chromosomal DNA of MJ233 strain as a template when a sucE1 gene is amplified using primers for amplifying the gene (SEQ ID NOS: 7 and 10 of the Sequence Listing) was obtained, and the strain was used as a sucE1-deleted strain in the following experiments. The resultant sucE1-deleted strain was named MJ233ΔldhΔsucE1.

Example 3

Construction of sucE1-Amplified Strain (A) Cloning of the sucE1 Gene

Figure 4:
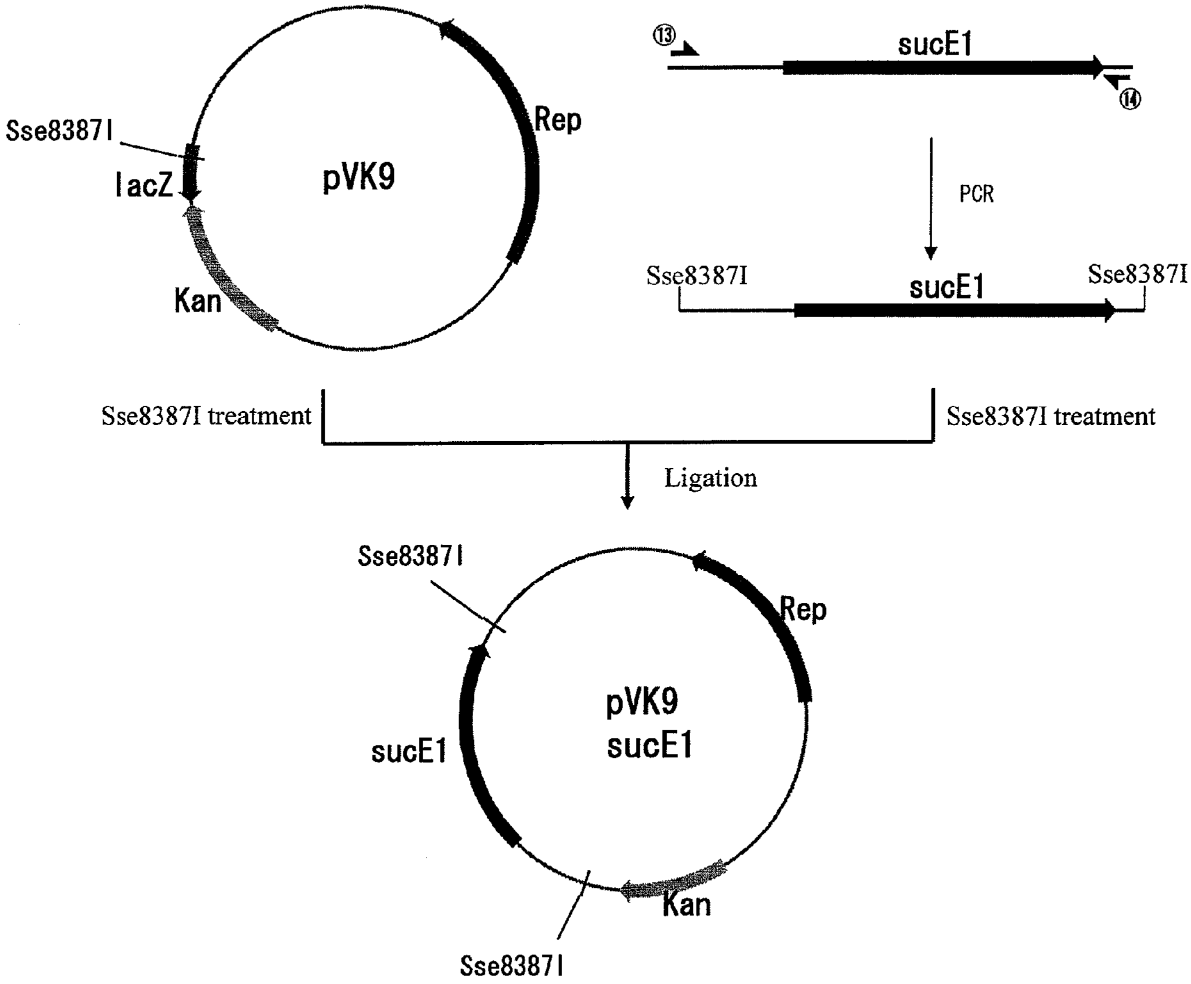
FIG. 4 A drawing showing the construction of a plasmid for amplifying sucE1. The numbers in the circles show the SEQ ID NOs of the primers.

A plasmid for amplifying a sucE1 gene derived from *Brevibacterium flavum* MJ233 strain was constructed as follows. PCR was performed using synthetic DNAs of SEQ ID NOS: 13 and 14 of the Sequence Listing, designed based on the sequence of nucleotides in the vicinity of NCgl2130 of *Corynebacterium glutamicum* ATCC13032 (Genbank Database Accession No. NC003450) as primers and using a genomic DNA of *Brevibacterium flavum* MJ233 strain as a template. PCR was carried out using Pyrobest DNA Polymerase (TaKaRa) such that one cycle of heat-retention at 94° C. for 3 minutes was performed, and then a cycle of denaturation at 94° C. for 30 seconds, annealing at 60° C. for 30 seconds, and elongation at 72° C. for 2.5 minutes was repeated 30 times, to thereby yield a PCR product of interest. The obtained PCR product was purified in accordance with a conventional method and digested with Sse8387I, followed by insertion into the Sse8387I site of pVK9. The obtained DNA was used to transform competent cells of *Escherichia coli* JM109 (TAKARA SHUZO CO., LTD.) and the transformed cells were applied on an LB medium containing 100 μM IPTG, 40 μg/ml X-Gal, and 25 μg/ml Km, followed by culture overnight. After that, appeared white colonies were separated, and a single colony was then isolated, thereby a transformant was obtained. Plasmid was extracted from the resultant transformant, and a plasmid having a structure shown in FIG. 4 was named pVK9sucE1. The pVK9 is a shuttle vector produced by inserting a region involved in autonomously replication in coryneform bacteria obtained by digesting pHK4 (JP 05-007491 A) with BamHI and KpnI and blunt-ending, into a pHSG299 (Takara Bio) which was digested with AvaII and blunt-ended.

(B) Creation of a sucE1-Amplified Strain

*Brevibacterium flavum* MJ233ΔLDH strain and MJ233ΔLDHΔsucE1 strain were transformed with pVK9sucE1 and pVK9 obtained in the item (A), respectively by the electrical pulse method, and the obtained cells were applied on a CM-Dex agar medium (5 g/L glucose, 10 g/L polypeptone, 10 g/L yeast extract, 1 g/L $KH_2PO_4$, 0.4 g/L $MgSO_4.7H_2O$, 0.01 g/L $FeSO_4.7H_2O$, 0.01 g/L $MnSO_4.7H_2O$, 3 g/L urea, and 1.2 g/L soybean hydrolysate, pH 7.5 (KOH), supplemented with 1.5% agar) containing 25 μg/ml kanamycin and cultured at 31.5° C. for about 24 hours. The appeared colonies were purified, and plasmids were extracted by a conventional method, followed by confirmation of introduction of the plasmid of interest.

Example 4

Production of Succinic Acid by the sucE1-Modified Strains

A strain obtained by introducing pVK9 or pVK9sucE1 into *Brevibacterium flavum* MJ233Δldh strain (WO 2005/021770) and a strain obtained by introducing pVK9 or pVK9sucE1 into MJ233ΔldhΔsucE1 strain were respectively cultured to produce succinic acid as follows. Bacterial cells obtained by culture in CM-Dex plate medium were inoculated into 20 ml of a seed culture medium (20 g/L glucose, 1.4 g/L $(NH_4)_2SO_4$, 0.5 g/L $KH_2PO_4$, 0.5 g/L $K_2HPO_4$, 0.5 g/L $MgSO_4.7H_2O$, 4 g/L urea, 0.02 g/L $FeSO_4.7H_2O$, 0.02 g/L $MnSO_4.7H_2O$, 200 μg/L biotin, 200 μg/L VB1.HCl, 1 g/L yeast extract, and 1 g/L casamino acid) and cultured with shaking under an aerobic condition at 31.5° C. in a Sakaguchi flask for about 8 hours.

After that, 700 μl of the seed culture solution was collected and immediately mixed with 700 μl of a main culture medium (dry-heat-sterilized magnesium carbonate was mixed at a final concentration of 143 g/L with a solution containing 200 g/L glucose and 30 g/L sodium sulfite which are subjected to filtration) in an eppendorf tube, followed by shaking culture at 31.5° C. 48 hours later, the culture was stopped, and the amount of produced succinic acid was analyzed by liquid chromatography. In the analysis, two Shim-pack SCR-102H (Simadzu) columns were serially connected, and samples were eluted with 5 mM p-toluenesulfonic acid at 40° C. The eluates were neutralized with 20 mM Bis-Tris solution containing 5 mM p-toluenesulfonic acid and 100 μM EDTA, and electrical conductivities were measured using CDD-10AD (Simadzu) to measure succinic acid amount. The results of evaluation for a plurality of samples of bacterial strains are shown in Table 1.

In the case of MJ233Δldh/pVK9sucE1, the amount of accumulated succinic acid was found to be about 1.5-fold larger than that in the case of MJ233Δldh/pVK9. The results revealed that enhancement of sucE1 expression is effective for fermentative production of succinic acid.

On the other hand, in the case of MJ233ΔldhΔsucE1/pVK9 strain, succinic acid was not accumulated at all. The fact means that a loss of a sucE1 gene from a succinic acid-producing bacterium significantly decreases the succinic acid-producing ability. In the case of the strain MJ233ΔldhΔsucE1/pVK9sucE1, obtained by complementing sucE1 into the sucE1-deleted strain with a plasmid, the amount of accumulated succinic acid was found to be higher than that in the case of MJ233ΔldhΔsucE1/pVK9. The copy number of pVK9 in a cell was about 10, and therefore when pVK9sucE1 is introduced into the MJ233ΔldhΔsucE1 strain, the expression level of sucE1 is higher than that in the case of a wild-type strain. The results show that enhancement of the expression of sucE1 is effective for production of succinic acid.

[Table 1]

TABLE 1

| Production of succinic acid by sucE1-modified strains | |
|---|---|
| Strain name | Succinic acid accumulation (g/L) |
| MJ233Δldh/pVK9 | 20.5 ± 2.00 |
| MJ233Δldh/pVK9sucE1 | 32.3 ± 0.12 |
| MJ233ΔldhΔsucE1/pVK9 | 0.0 |
| MJ233ΔldhΔsucE1/pVK9sucE1 | 32.5 ± 0.30 |

INDUSTRIAL APPLICABILITY

According to the production process of the present invention, succinic acid can be produced quickly at high efficiency. The obtained succinic acid can be used as food additives, drugs, cosmetics, and so on. In addition, by using the obtained succinic acid as a raw material, a succinic acid-containing polymer can be also produced by performing a polymerization reaction.

The invention claimed is:

1. A method for producing succinic acid, comprising: allowing (i) a bacterium which is modified so that expression of a sucE1 gene is enhanced by increasing the copy number of the gene or by modifying an expression regulatory sequence of the gene; or (ii) treated cells thereof to act on an organic raw material in a reaction solution containing carbonate ion, bicarbonate ion, or carbon dioxide, to produce succinic acid; and collecting the succinic acid;

wherein the sucE1 gene encodes a protein having homology of not less than 95% to the whole amino acid sequence of SEQ ID NO: 16.

2. The method according to claim 1, wherein the bacterium is selected from the group consisting of coryneform bacterium, *Bacillus* bacterium, and *Rhizobium* bacterium.

3. The method according to claim 1, wherein the bacterium is further modified so that lactate dehydrogenase activity is decreased to 10% or less as compared to an unmodified strain.

4. The method according to claim 1, wherein the bacterium is further modified so that pyruvate carboxylase activity is enhanced.

5. A method for producing a succinic acid-containing polymer, comprising:

producing succinic acid by the method according to claim 1; and polymerizing the obtained succinic acid.

* * * * *

SEQUENCE LISTING

<160> NUMBER OF SEQ ID NOS: 24

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
cgggatcctt tttaacccat caca 24

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
gaagatcttc aaaaggttag gaatacggt 29

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
ccttttgaag atcgaccagt tgg 23

<210> SEQ ID NO 4
<211> LENGTH: 44
<212> TYPE: DNA
<213> ORGANISM: Artificial
<220> FEATURE:
<223> OTHER INFORMATION: primer

<400> SEQUENCE: 4
tacctggaat gctgttttcc cagggatcgc agtggtgagt aacc 44

<210> SEQ ID NO 5
<211> LENGTH: 28
<212> TYPE: DNA
<213> ORGANISM: Artificial
<220> FEATURE:
<223> OTHER INFORMATION: primer -continued

<400> SEQUENCE: 5
cctgggaaaa cagcattcca ggtattag 28

<210> SEQ ID NO 6
<211> LENGTH: 23
<212> TYPE: DNA
<213> ORGANISM: Artificial
<220> FEATURE:
<223> OTHER INFORMATION: primer

<400> SEQUENCE: 6
tgcaggtcga ctctagagga tcc 23

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
gggggatccg tgctctttct acacctctt 29

<210> SEQ ID NO 8
<211> LENGTH: 40
<212> TYPE: DNA
<213> ORGANISM: Artificial
<220> FEATURE:
<223> OTHER INFORMATION: primer

<400> SEQUENCE: 8
gcgcttaagg ggtcaatgct ccattcatga tctcatggat 40

<210> SEQ ID NO 9
<211> LENGTH: 40
<212> TYPE: DNA
<213> ORGANISM: Artificial
<220> FEATURE:
<223> OTHER INFORMATION: primer

<400> SEQUENCE: 9
atccatgaga tcatgaatgg agcattgacc ccttaagcgc 40

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10
gggggatcct cctgggttgg cttaccggt 29

<210> SEQ ID NO 11
<211> LENGTH: 29
<212> TYPE: DNA
<213> ORGANISM: Artificial
<220> FEATURE:
<223> OTHER INFORMATION: primer

<400> SEQUENCE: 11
gggggatcca ttttcgcggt ttcctcaca 29

-continued

```
<210> SEQ ID NO 12
<211> LENGTH: 29
<212> TYPE: DNA
<213> ORGANISM: Artificial
<220> FEATURE:
<223> OTHER INFORMATION: primer

<400> SEQUENCE: 12

gggggatcct ggatgcagag gaacgtgtg                                   29


<210> SEQ ID NO 13
<211> LENGTH: 33
<212> TYPE: DNA
<213> ORGANISM: Artificial
<220> FEATURE:
<223> OTHER INFORMATION: primer

<400> SEQUENCE: 13

gggcctgcag gaccaagacc gctgttgcag tga                              33


<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14

gggcctgcag ggtattcaca ccagccccaa t                                31


<210> SEQ ID NO 15
<211> LENGTH: 2330
<212> TYPE: DNA
<213> ORGANISM: Brevibacterium flavum
<220> FEATURE:
<221> NAME/KEY: CDS
<222> LOCATION: (571)..(2187)

<400> SEQUENCE: 15

gaccaagacc gctgttgcag tgaccactca gatggatgca gtgcaccgcg tcattggtct     60

gtgtggtgtt gtgctggtcg gcgagggctc ccctcaccgc ctgaagccaa tgcttgcgca    120

gcaaaagaag cgcctgaacc gcgtggcacc tggtgttccg gtgtatgaaa tcatcacggg    180

caacggcgaa ggccagaccc ctatcgcgaa gctgcagcgt gaactggtca agctgcctcg    240

caactacaag aagaacgacg tcgctgccct ggccgctcgc attgaggcta tggacaatgt    300

cggaaacgct cctggcggat ctttgcctaa gggtccattg ccaaagggcg caagcatgtc    360

cggtatgaac cgccgtgctc gccgacaggc tgaacgcagg ggcgaggctt aaagcctttt    420

cgctttcgcg tcggcgccga agttttttaa aaagccgcac ttcaccaact tggatggggt    480

gcggtttttg cgtgctctgg cttagggaac gtggccagtt ccacatcaaa taacgcagaa    540

gtagtactta atccatgaga tcatgaatgg gtg agc ttc ctt gta gaa aat caa     594
                                  Val Ser Phe Leu Val Glu Asn Gln
                                  1               5

tta ctc gcg ttg gtt gtc atc atg acg gtc gga cta ttg ctc ggc cgc      642
Leu Leu Ala Leu Val Val Ile Met Thr Val Gly Leu Leu Leu Gly Arg
    10                  15                  20

atc aaa att ttc ggg ttc cgc ctc ggt gtg gcc gct gta ttg ttt gtc      690
Ile Lys Ile Phe Gly Phe Arg Leu Gly Val Ala Ala Val Leu Phe Val
25                  30                  35                  40

ggt ctg gcg ctg tcc acc att gag ccg gat att tcc gtc ccg ccg ctc      738
Gly Leu Ala Leu Ser Thr Ile Glu Pro Asp Ile Ser Val Pro Pro Leu
                45                  50                  55
```

-continued

```
att tat gtt gtt gga ctg tca ctt ttt gtc tac acc atc gga ctg gag      786
Ile Tyr Val Val Gly Leu Ser Leu Phe Val Tyr Thr Ile Gly Leu Glu
            60                  65                  70

gcc ggc ccc gga ttc ttc acc tcc atg aaa acc aca ggt ctg cgc aac      834
Ala Gly Pro Gly Phe Phe Thr Ser Met Lys Thr Thr Gly Leu Arg Asn
        75                  80                  85

aac gca ctg acc ttg ggc gcc atc atc gcc acc acg gca ctc gca tgg      882
Asn Ala Leu Thr Leu Gly Ala Ile Ile Ala Thr Thr Ala Leu Ala Trp
    90                  95                  100

gca ctc atc acc gtt ttc aac atc gat gcc gcc tcc ggt gcc ggt atg      930
Ala Leu Ile Thr Val Phe Asn Ile Asp Ala Ala Ser Gly Ala Gly Met
105                 110                 115                 120

ctc acc ggc gcg ctc acc aat acc cca gcc atg gcc gcg gtt gtt gac      978
Leu Thr Gly Ala Leu Thr Asn Thr Pro Ala Met Ala Ala Val Val Asp
                125                 130                 135

gca ctg cct tcg ctt atc gac gac acc ggc cag ctt cac atc atc gcc     1026
Ala Leu Pro Ser Leu Ile Asp Asp Thr Gly Gln Leu His Ile Ile Ala
            140                 145                 150

gag ttg ccc gtc gtc gca tat tcc ttg gca tac ccc ctc gga gtg ctc     1074
Glu Leu Pro Val Val Ala Tyr Ser Leu Ala Tyr Pro Leu Gly Val Leu
        155                 160                 165

atc gtt att ctc tcc atc gcg atc ttc agc tct gtg ttc aaa gtg gat     1122
Ile Val Ile Leu Ser Ile Ala Ile Phe Ser Ser Val Phe Lys Val Asp
    170                 175                 180

cac aat aaa gag gcc gaa gaa gca ggt gtc gcg gtc cag gaa ctc aaa     1170
His Asn Lys Glu Ala Glu Glu Ala Gly Val Ala Val Gln Glu Leu Lys
185                 190                 195                 200

ggc cgc cgc atc cgc gtc acc gtc gct gat ctt cca gcc ctg gag aat     1218
Gly Arg Arg Ile Arg Val Thr Val Ala Asp Leu Pro Ala Leu Glu Asn
                205                 210                 215

atc cca gag ctg ctc aat ctc cac gtc att gtg tcc cgc gtg gaa cga     1266
Ile Pro Glu Leu Leu Asn Leu His Val Ile Val Ser Arg Val Glu Arg
            220                 225                 230

gac ggt gag caa ttc ata ccg ctt tat ggc gaa cac gca cgc atc ggc     1314
Asp Gly Glu Gln Phe Ile Pro Leu Tyr Gly Glu His Ala Arg Ile Gly
        235                 240                 245

gat gtc tta aca gtg gtg ggt gcc gat gaa gaa ctc aac cgc gcg gaa     1362
Asp Val Leu Thr Val Val Gly Ala Asp Glu Glu Leu Asn Arg Ala Glu
    250                 255                 260

aaa gcc atc ggt gaa ctc atc gac ggc gac ccc tac agc gat gtg gaa     1410
Lys Ala Ile Gly Glu Leu Ile Asp Gly Asp Pro Tyr Ser Asp Val Glu
265                 270                 275                 280

ctt gat tac cga cgc atc ttc gtc tca aac aca gaa gtc gtg ggc act     1458
Leu Asp Tyr Arg Arg Ile Phe Val Ser Asn Thr Glu Val Val Gly Thr
                285                 290                 295

ccc cta tcc aag ctc caa cca cta ttt aaa gac atg ctg atc acc cgt     1506
Pro Leu Ser Lys Leu Gln Pro Leu Phe Lys Asp Met Leu Ile Thr Arg
            300                 305                 310

atc agg cgc ggc gac aca gat ttg gtg gcc tcc ccc gac atg act ttg     1554
Ile Arg Arg Gly Asp Thr Asp Leu Val Ala Ser Pro Asp Met Thr Leu
        315                 320                 325

cag cta ggt gat cgt gtc cgc gtt gtc gca cca aca gag aag ctc cgc     1602
Gln Leu Gly Asp Arg Val Arg Val Val Ala Pro Thr Glu Lys Leu Arg
    330                 335                 340

gaa gca acc cga cta ctg ggc gat tcc tac aaa aaa ctc tcc gat ttc     1650
Glu Ala Thr Arg Leu Leu Gly Asp Ser Tyr Lys Lys Leu Ser Asp Phe
345                 350                 355                 360

aac ctg ctc ccc ctc gct gcc ggc ctc atg atc ggt gtg ctt gtc ggc     1698
Asn Leu Leu Pro Leu Ala Ala Gly Leu Met Ile Gly Val Leu Val Gly
                365                 370                 375
```

-continued

```
atg gta gaa ttc cca cta cca ggt gga agc tcc ctg aaa ctg ggt aac      1746
Met Val Glu Phe Pro Leu Pro Gly Gly Ser Ser Leu Lys Leu Gly Asn
            380                 385                 390

gca ggt gga ccg cta gtt gtt gcg ctg ctg ctc ggc atg att aat cgc      1794
Ala Gly Gly Pro Leu Val Val Ala Leu Leu Leu Gly Met Ile Asn Arg
        395                 400                 405

aca ggc aag ttc gtc tgg caa atc ccc tac gga gca aac ctt gcc ctt      1842
Thr Gly Lys Phe Val Trp Gln Ile Pro Tyr Gly Ala Asn Leu Ala Leu
    410                 415                 420

cgc caa ctg ggc atc aca cta ttt ttg gct gcc atc ggt acc tca gcg      1890
Arg Gln Leu Gly Ile Thr Leu Phe Leu Ala Ala Ile Gly Thr Ser Ala
425                 430                 435                 440

ggc gca gga ttt cga tca gcg atc agc gac ccc caa tca ctc acc atc      1938
Gly Ala Gly Phe Arg Ser Ala Ile Ser Asp Pro Gln Ser Leu Thr Ile
                445                 450                 455

atc ggc ttc ggt gcg ctg ctc act ttg ttc atc tcc atc acg gtc ctg      1986
Ile Gly Phe Gly Ala Leu Leu Thr Leu Phe Ile Ser Ile Thr Val Leu
            460                 465                 470

ttc gtt ggc cac aaa ctg atg aaa atc ccc ttc ggt gaa acc gct ggc      2034
Phe Val Gly His Lys Leu Met Lys Ile Pro Phe Gly Glu Thr Ala Gly
        475                 480                 485

atc ctc gcc ggt acg caa acc cac cct gct gtg ctg agt tat gtg tca      2082
Ile Leu Ala Gly Thr Gln Thr His Pro Ala Val Leu Ser Tyr Val Ser
    490                 495                 500

gat gcc tcc cgc aac gag ctc cct gcc atg ggt tat acc tct gtg tat      2130
Asp Ala Ser Arg Asn Glu Leu Pro Ala Met Gly Tyr Thr Ser Val Tyr
505                 510                 515                 520

ccg ctg gcg atg atc gca aag atc ctg gcc gcc caa acg ttg ttg ttc      2178
Pro Leu Ala Met Ile Ala Lys Ile Leu Ala Ala Gln Thr Leu Leu Phe
                525                 530                 535

cta ctt atc tagcattgac cccttaagcg cagaaggcga tttaaggggt             2227
Leu Leu Ile

tgggttttcc cgatgactag ttggtccaga gcgtgtattt gaggccctta ggggcgattc   2287

tggggctgat gtttttgtgt ccattggggc tggtgtgaat acc                     2330


<210> SEQ ID NO 16
<211> LENGTH: 539
<212> TYPE: PRT
<213> ORGANISM: Brevibacterium flavum

<400> SEQUENCE: 16

Met Ser Phe Leu Val Glu Asn Gln Leu Leu Ala Leu Val Val Ile Met
1               5                   10                  15

Thr Val Gly Leu Leu Leu Gly Arg Ile Lys Ile Phe Gly Phe Arg Leu
            20                  25                  30

Gly Val Ala Ala Val Leu Phe Val Gly Leu Ala Leu Ser Thr Ile Glu
        35                  40                  45

Pro Asp Ile Ser Val Pro Pro Leu Ile Tyr Val Val Gly Leu Ser Leu
    50                  55                  60

Phe Val Tyr Thr Ile Gly Leu Glu Ala Gly Pro Gly Phe Phe Thr Ser
65                  70                  75                  80

Met Lys Thr Thr Gly Leu Arg Asn Asn Ala Leu Thr Leu Gly Ala Ile
                85                  90                  95

Ile Ala Thr Thr Ala Leu Ala Trp Ala Leu Ile Thr Val Phe Asn Ile
            100                 105                 110

Asp Ala Ala Ser Gly Ala Gly Met Leu Thr Gly Ala Leu Thr Asn Thr
        115                 120                 125
```

-continued

```
Pro Ala Met Ala Ala Val Val Asp Ala Leu Pro Ser Leu Ile Asp Asp
    130                 135                 140

Thr Gly Gln Leu His Ile Ile Ala Glu Leu Pro Val Val Ala Tyr Ser
145                 150                 155                 160

Leu Ala Tyr Pro Leu Gly Val Leu Ile Val Ile Leu Ser Ile Ala Ile
                165                 170                 175

Phe Ser Ser Val Phe Lys Val Asp His Asn Lys Glu Ala Glu Glu Ala
            180                 185                 190

Gly Val Ala Val Gln Glu Leu Lys Gly Arg Arg Ile Arg Val Thr Val
        195                 200                 205

Ala Asp Leu Pro Ala Leu Glu Asn Ile Pro Glu Leu Leu Asn Leu His
    210                 215                 220

Val Ile Val Ser Arg Val Glu Arg Asp Gly Glu Gln Phe Ile Pro Leu
225                 230                 235                 240

Tyr Gly Glu His Ala Arg Ile Gly Asp Val Leu Thr Val Val Gly Ala
                245                 250                 255

Asp Glu Glu Leu Asn Arg Ala Glu Lys Ala Ile Gly Glu Leu Ile Asp
            260                 265                 270

Gly Asp Pro Tyr Ser Asp Val Glu Leu Asp Tyr Arg Arg Ile Phe Val
        275                 280                 285

Ser Asn Thr Glu Val Val Gly Thr Pro Leu Ser Lys Leu Gln Pro Leu
    290                 295                 300

Phe Lys Asp Met Leu Ile Thr Arg Ile Arg Arg Gly Asp Thr Asp Leu
305                 310                 315                 320

Val Ala Ser Pro Asp Met Thr Leu Gln Leu Gly Asp Arg Val Arg Val
                325                 330                 335

Val Ala Pro Thr Glu Lys Leu Arg Glu Ala Thr Arg Leu Leu Gly Asp
            340                 345                 350

Ser Tyr Lys Lys Leu Ser Asp Phe Asn Leu Leu Pro Leu Ala Ala Gly
        355                 360                 365

Leu Met Ile Gly Val Leu Val Gly Met Val Glu Phe Pro Leu Pro Gly
    370                 375                 380

Gly Ser Ser Leu Lys Leu Gly Asn Ala Gly Gly Pro Leu Val Val Ala
385                 390                 395                 400

Leu Leu Leu Gly Met Ile Asn Arg Thr Gly Lys Phe Val Trp Gln Ile
                405                 410                 415

Pro Tyr Gly Ala Asn Leu Ala Leu Arg Gln Leu Gly Ile Thr Leu Phe
            420                 425                 430

Leu Ala Ala Ile Gly Thr Ser Ala Gly Ala Gly Phe Arg Ser Ala Ile
        435                 440                 445

Ser Asp Pro Gln Ser Leu Thr Ile Ile Gly Phe Gly Ala Leu Leu Thr
    450                 455                 460

Leu Phe Ile Ser Ile Thr Val Leu Phe Val Gly His Lys Leu Met Lys
465                 470                 475                 480

Ile Pro Phe Gly Glu Thr Ala Gly Ile Leu Ala Gly Thr Gln Thr His
                485                 490                 495

Pro Ala Val Leu Ser Tyr Val Ser Asp Ala Ser Arg Asn Glu Leu Pro
            500                 505                 510

Ala Met Gly Tyr Thr Ser Val Tyr Pro Leu Ala Met Ile Ala Lys Ile
        515                 520                 525

Leu Ala Ala Gln Thr Leu Leu Phe Leu Leu Ile
    530                 535
```

-continued

```
<210> SEQ ID NO 17
<211> LENGTH: 1620
<212> TYPE: DNA
<213> ORGANISM: Corynebacterium glutamicum
<220> FEATURE:
<221> NAME/KEY: CDS
<222> LOCATION: (1)..(1617)

<400> SEQUENCE: 17

gtg agc ttc ctt gta gaa aat caa tta ctc gcg ttg gtt gtc atc atg       48
Val Ser Phe Leu Val Glu Asn Gln Leu Leu Ala Leu Val Val Ile Met
1               5                   10                  15

acg gtc gga cta ttg ctc ggc cgc atc aaa att ttc ggg ttc cgt ctc       96
Thr Val Gly Leu Leu Leu Gly Arg Ile Lys Ile Phe Gly Phe Arg Leu
            20                  25                  30

ggc gtc gcc gct gta ctg ttt gta ggt cta gcg cta tcc acc att gag      144
Gly Val Ala Ala Val Leu Phe Val Gly Leu Ala Leu Ser Thr Ile Glu
        35                  40                  45

ccg gat att tcc gtc cca tcc ctc att tac gtg gtt gga ctg tcg ctt      192
Pro Asp Ile Ser Val Pro Ser Leu Ile Tyr Val Val Gly Leu Ser Leu
    50                  55                  60

ttt gtc tac acg atc ggt ctg gaa gcc ggc cct gga ttc ttc acc tcc      240
Phe Val Tyr Thr Ile Gly Leu Glu Ala Gly Pro Gly Phe Phe Thr Ser
65                  70                  75                  80

atg aaa acc act ggt ctg cgc aac aac gca ctg acc ttg ggc gcc atc      288
Met Lys Thr Thr Gly Leu Arg Asn Asn Ala Leu Thr Leu Gly Ala Ile
                85                  90                  95

atc gcc acc acg gca ctc gca tgg gca ctc atc aca gtt ttg aac atc      336
Ile Ala Thr Thr Ala Leu Ala Trp Ala Leu Ile Thr Val Leu Asn Ile
            100                 105                 110

gat gcc gcc tcc ggc gcc ggc atg ctc acc ggc gcg ctc acc aac acc      384
Asp Ala Ala Ser Gly Ala Gly Met Leu Thr Gly Ala Leu Thr Asn Thr
        115                 120                 125

cca gcc atg gcc gca gtt gtt gac gca ctt cct tcg ctt atc gac gac      432
Pro Ala Met Ala Ala Val Val Asp Ala Leu Pro Ser Leu Ile Asp Asp
    130                 135                 140

acc ggc cag ctt cac ctc atc gcc gag ctg ccc gtc gtc gca tat tcc      480
Thr Gly Gln Leu His Leu Ile Ala Glu Leu Pro Val Val Ala Tyr Ser
145                 150                 155                 160

ttg gca tac ccc ctc ggt gtg ctc atc gtt att ctc tcc atc gcc atc      528
Leu Ala Tyr Pro Leu Gly Val Leu Ile Val Ile Leu Ser Ile Ala Ile
                165                 170                 175

ttc agc tct gtg ttc aaa gtc gac cac aac aaa gaa gcc gaa gaa gcg      576
Phe Ser Ser Val Phe Lys Val Asp His Asn Lys Glu Ala Glu Glu Ala
            180                 185                 190

ggc gtt gcg gtc cag gaa ctc aaa ggc cgt cgc atc cgc gtc acc gtc      624
Gly Val Ala Val Gln Glu Leu Lys Gly Arg Arg Ile Arg Val Thr Val
        195                 200                 205

gct gat ctt cca gcc ctg gag aac atc cca gag ctg ctc aac ctc cac      672
Ala Asp Leu Pro Ala Leu Glu Asn Ile Pro Glu Leu Leu Asn Leu His
    210                 215                 220

gtc att gtg tcc cga gtg gaa cga gac ggt gag caa ttc atc ccg ctt      720
Val Ile Val Ser Arg Val Glu Arg Asp Gly Glu Gln Phe Ile Pro Leu
225                 230                 235                 240

tat ggc gaa cac gca cgc atc ggc gat gtc tta aca gtg gtg ggt gcc      768
Tyr Gly Glu His Ala Arg Ile Gly Asp Val Leu Thr Val Val Gly Ala
                245                 250                 255

gat gaa gaa ctc aac cgc gcg gaa aaa gcc atc ggt gaa ctc att gac      816
Asp Glu Glu Leu Asn Arg Ala Glu Lys Ala Ile Gly Glu Leu Ile Asp
            260                 265                 270
```

-continued

```
ggc gac ccc tac agc aat gtg gaa ctt gat tac cga cgc atc ttc gtc      864
Gly Asp Pro Tyr Ser Asn Val Glu Leu Asp Tyr Arg Arg Ile Phe Val
        275                 280                 285

tca aac aca gca gtc gtg ggc act ccc cta tcc aag ctc cag cca ctg      912
Ser Asn Thr Ala Val Val Gly Thr Pro Leu Ser Lys Leu Gln Pro Leu
    290                 295                 300

ttt aaa gac atg ctg atc acc cgc atc agg cgc ggc gac aca gat ttg      960
Phe Lys Asp Met Leu Ile Thr Arg Ile Arg Arg Gly Asp Thr Asp Leu
305                 310                 315                 320

gtg gcc tcc tcc gac atg act ttg cag ctc ggt gac cgt gtc cgc gtt     1008
Val Ala Ser Ser Asp Met Thr Leu Gln Leu Gly Asp Arg Val Arg Val
                325                 330                 335

gtc gca cca gca gaa aaa ctc cgc gaa gca acc caa ttg ctc ggc gat     1056
Val Ala Pro Ala Glu Lys Leu Arg Glu Ala Thr Gln Leu Leu Gly Asp
            340                 345                 350

tcc tac aag aaa ctc tcc gat ttc aac ctg ctc cca ctc gct gcc ggc     1104
Ser Tyr Lys Lys Leu Ser Asp Phe Asn Leu Leu Pro Leu Ala Ala Gly
        355                 360                 365

ctc atg atc ggt gtg ctt gtc ggc atg gtg gag ttc cca cta cca ggt     1152
Leu Met Ile Gly Val Leu Val Gly Met Val Glu Phe Pro Leu Pro Gly
    370                 375                 380

gga agc tcc ctg aaa ctg ggt aac gca ggt gga ccg cta gtt gtt gcg     1200
Gly Ser Ser Leu Lys Leu Gly Asn Ala Gly Gly Pro Leu Val Val Ala
385                 390                 395                 400

ctg ctg ctc ggc atg atc aat cgc aca ggc aag ttc gtc tgg caa atc     1248
Leu Leu Leu Gly Met Ile Asn Arg Thr Gly Lys Phe Val Trp Gln Ile
                405                 410                 415

ccc tac gga gca aac ctt gcc ctt cgc caa ctg ggc atc aca cta ttt     1296
Pro Tyr Gly Ala Asn Leu Ala Leu Arg Gln Leu Gly Ile Thr Leu Phe
            420                 425                 430

ttg gct gcc atc ggt acc tca gcg ggc gca gga ttt cga tca gcg atc     1344
Leu Ala Ala Ile Gly Thr Ser Ala Gly Ala Gly Phe Arg Ser Ala Ile
        435                 440                 445

agc gac ccc caa tca ctc acc atc atc ggc ttc ggt gcg ctg ctc act     1392
Ser Asp Pro Gln Ser Leu Thr Ile Ile Gly Phe Gly Ala Leu Leu Thr
    450                 455                 460

ttg ttc atc tcc atc acg gtg ctg ttc gtt ggc cac aaa ctg atg aaa     1440
Leu Phe Ile Ser Ile Thr Val Leu Phe Val Gly His Lys Leu Met Lys
465                 470                 475                 480

atc ccc ttc ggt gaa acc gct ggc atc ctc gcc ggt acg caa acc cac     1488
Ile Pro Phe Gly Glu Thr Ala Gly Ile Leu Ala Gly Thr Gln Thr His
                485                 490                 495

cct gct gtg ctg agt tat gtg tca gat gcc tcc cgc aac gag ctc cct     1536
Pro Ala Val Leu Ser Tyr Val Ser Asp Ala Ser Arg Asn Glu Leu Pro
            500                 505                 510

gcc atg ggt tat acc tct gtg tat ccg ctg gcg atg atc gca aag atc     1584
Ala Met Gly Tyr Thr Ser Val Tyr Pro Leu Ala Met Ile Ala Lys Ile
        515                 520                 525

ctg gcc gcc caa acg ttg ttg ttc cta ctt atc tag                     1620
Leu Ala Ala Gln Thr Leu Leu Phe Leu Leu Ile
    530                 535
```

<210> SEQ ID NO 18
<211> LENGTH: 539
<212> TYPE: PRT
<213> ORGANISM: Corynebacterium glutamicum -continued

<400> SEQUENCE: 18

Met Ser Phe Leu Val Glu Asn Gln Leu Leu Ala Leu Val Val Ile Met
1 5 10 15

Thr Val Gly Leu Leu Leu Gly Arg Ile Lys Ile Phe Gly Phe Arg Leu
20 25 30

Gly Val Ala Ala Val Leu Phe Val Gly Leu Ala Leu Ser Thr Ile Glu
35 40 45

Pro Asp Ile Ser Val Pro Ser Leu Ile Tyr Val Val Gly Leu Ser Leu
50 55 60

Phe Val Tyr Thr Ile Gly Leu Glu Ala Gly Pro Gly Phe Phe Thr Ser
65 70 75 80

Met Lys Thr Thr Gly Leu Arg Asn Asn Ala Leu Thr Leu Gly Ala Ile
85 90 95

Ile Ala Thr Thr Ala Leu Ala Trp Ala Leu Ile Thr Val Leu Asn Ile
100 105 110

Asp Ala Ala Ser Gly Ala Gly Met Leu Thr Gly Ala Leu Thr Asn Thr
115 120 125

Pro Ala Met Ala Ala Val Val Asp Ala Leu Pro Ser Leu Ile Asp Asp
130 135 140

Thr Gly Gln Leu His Leu Ile Ala Glu Leu Pro Val Val Ala Tyr Ser
145 150 155 160

Leu Ala Tyr Pro Leu Gly Val Leu Ile Val Ile Leu Ser Ile Ala Ile
165 170 175

Phe Ser Ser Val Phe Lys Val Asp His Asn Lys Glu Ala Glu Glu Ala
180 185 190

Gly Val Ala Val Gln Glu Leu Lys Gly Arg Arg Ile Arg Val Thr Val
195 200 205

Ala Asp Leu Pro Ala Leu Glu Asn Ile Pro Glu Leu Leu Asn Leu His
210 215 220

Val Ile Val Ser Arg Val Glu Arg Asp Gly Glu Gln Phe Ile Pro Leu
225 230 235 240

Tyr Gly Glu His Ala Arg Ile Gly Asp Val Leu Thr Val Val Gly Ala
245 250 255

Asp Glu Glu Leu Asn Arg Ala Glu Lys Ala Ile Gly Glu Leu Ile Asp
260 265 270

Gly Asp Pro Tyr Ser Asn Val Glu Leu Asp Tyr Arg Arg Ile Phe Val
275 280 285

Ser Asn Thr Ala Val Val Gly Thr Pro Leu Ser Lys Leu Gln Pro Leu
290 295 300

Phe Lys Asp Met Leu Ile Thr Arg Ile Arg Arg Gly Asp Thr Asp Leu
305 310 315 320

Val Ala Ser Ser Asp Met Thr Leu Gln Leu Gly Asp Arg Val Arg Val
325 330 335

Val Ala Pro Ala Glu Lys Leu Arg Glu Ala Thr Gln Leu Leu Gly Asp
340 345 350

Ser Tyr Lys Lys Leu Ser Asp Phe Asn Leu Leu Pro Leu Ala Ala Gly
355 360 365

Leu Met Ile Gly Val Leu Val Gly Met Val Glu Phe Pro Leu Pro Gly
370 375 380

Gly Ser Ser Leu Lys Leu Gly Asn Ala Gly Gly Pro Leu Val Val Ala
385 390 395 400

Leu Leu Leu Gly Met Ile Asn Arg Thr Gly Lys Phe Val Trp Gln Ile
405 410 415

-continued

```
Pro Tyr Gly Ala Asn Leu Ala Leu Arg Gln Leu Gly Ile Thr Leu Phe
            420                 425                 430

Leu Ala Ala Ile Gly Thr Ser Ala Gly Ala Gly Phe Arg Ser Ala Ile
        435                 440                 445

Ser Asp Pro Gln Ser Leu Thr Ile Ile Gly Phe Gly Ala Leu Leu Thr
    450                 455                 460

Leu Phe Ile Ser Ile Thr Val Leu Phe Val Gly His Lys Leu Met Lys
465                 470                 475                 480

Ile Pro Phe Gly Glu Thr Ala Gly Ile Leu Ala Gly Thr Gln Thr His
                485                 490                 495

Pro Ala Val Leu Ser Tyr Val Ser Asp Ala Ser Arg Asn Glu Leu Pro
            500                 505                 510

Ala Met Gly Tyr Thr Ser Val Tyr Pro Leu Ala Met Ile Ala Lys Ile
        515                 520                 525

Leu Ala Ala Gln Thr Leu Leu Phe Leu Leu Ile
    530                 535


<210> SEQ ID NO 19
<211> LENGTH: 1629
<212> TYPE: DNA
<213> ORGANISM: Corynebacterium accolens
<220> FEATURE:
<221> NAME/KEY: CDS
<222> LOCATION: (1)..(1626)

<400> SEQUENCE: 19

gtg agc att ttc gtg gaa aat cag ttg ttg gcc ctg gtg gcc atc atg       48
Val Ser Ile Phe Val Glu Asn Gln Leu Leu Ala Leu Val Ala Ile Met
1               5                   10                  15

ggt atc ggt ctg ttg ctc ggc cgg atc agg ttc ttc ggg ttc cgg ctc       96
Gly Ile Gly Leu Leu Leu Gly Arg Ile Arg Phe Phe Gly Phe Arg Leu
            20                  25                  30

ggg gtg gcg gcg gtg ttg ttc gtg ggt ctg gcc ttc tcc acc atc gaa      144
Gly Val Ala Ala Val Leu Phe Val Gly Leu Ala Phe Ser Thr Ile Glu
        35                  40                  45

ccg gac atc acg gtg cct ccc ctg atc tac gtg gtg ggc ctg gcc ctg      192
Pro Asp Ile Thr Val Pro Pro Leu Ile Tyr Val Val Gly Leu Ala Leu
    50                  55                  60

ttt gtg tac acc atc ggg ctg gag gcc ggc cgt gac ttc ttc agg tcg      240
Phe Val Tyr Thr Ile Gly Leu Glu Ala Gly Arg Asp Phe Phe Arg Ser
65                  70                  75                  80

ctg cgg tcc acc ggc ctg cgt aac aac ggg ctg gcc ctc ggt gcc atc      288
Leu Arg Ser Thr Gly Leu Arg Asn Asn Gly Leu Ala Leu Gly Ala Ile
                85                  90                  95

atc gcc acc acc gcg atc gcc tgg gtg gtc atc aag gcg ctg ggc ctg      336
Ile Ala Thr Thr Ala Ile Ala Trp Val Val Ile Lys Ala Leu Gly Leu
            100                 105                 110

gca ccc gcg acg ggt gcc ggc atg ttg acc ggt gcg ctg acc aac acc      384
Ala Pro Ala Thr Gly Ala Gly Met Leu Thr Gly Ala Leu Thr Asn Thr
        115                 120                 125

ccg gcg atg gcg gcg gtg gtc gac gcc cta ccg gcg ctt atc gac gac      432
Pro Ala Met Ala Ala Val Val Asp Ala Leu Pro Ala Leu Ile Asp Asp
    130                 135                 140

aac ccc acc gac gca gca cgc atc ctg gag ctg cct gtg gtg gcc tat      480
Asn Pro Thr Asp Ala Ala Arg Ile Leu Glu Leu Pro Val Val Ala Tyr
145                 150                 155                 160

tcc ctc acc tac ccg ctc ggt gtc ctg gtg gtg atc ctc acg atc gcg      528
Ser Leu Thr Tyr Pro Leu Gly Val Leu Val Val Ile Leu Thr Ile Ala
                165                 170                 175
```

-continued

```
gtc tgc ggg ggc ctg ttc aag gtc aac cat gag aag gag gcg aag aat      576
Val Cys Gly Gly Leu Phe Lys Val Asn His Glu Lys Glu Ala Lys Asn
            180                 185                 190

gcc ggc gtg gcc gtt cag gag ctg acg gga cgc cgt gtc cgg gtc acc      624
Ala Gly Val Ala Val Gln Glu Leu Thr Gly Arg Arg Val Arg Val Thr
        195                 200                 205

cgg gat gat ctg ccc gcc atc agc aat atc ccg gaa ctg ctg gac ctg      672
Arg Asp Asp Leu Pro Ala Ile Ser Asn Ile Pro Glu Leu Leu Asp Leu
    210                 215                 220

gag gtc atc gtc tcc cgt gtg gag cgc cgg ggg cag cat gac cag ttc      720
Glu Val Ile Val Ser Arg Val Glu Arg Arg Gly Gln His Asp Gln Phe
225                 230                 235                 240

atc ccc gag gag ggt gat cgc acc cgg ttg ggt gac att ctc acc gtg      768
Ile Pro Glu Glu Gly Asp Arg Thr Arg Leu Gly Asp Ile Leu Thr Val
                245                 250                 255

gtg ggc tcc gat gat gag ctc gag cgc gcg gtg ggt ctg ctc ggc gaa      816
Val Gly Ser Asp Asp Glu Leu Glu Arg Ala Val Gly Leu Leu Gly Glu
            260                 265                 270

ttc gtc gac ggc cat cca tac agc gat atc gat ctg gat tac cgc agg      864
Phe Val Asp Gly His Pro Tyr Ser Asp Ile Asp Leu Asp Tyr Arg Arg
        275                 280                 285

atc ttc gtc tct gat gaa tcc atg gtc ggt gtg ccc ttg gcg aaa ctg      912
Ile Phe Val Ser Asp Glu Ser Met Val Gly Val Pro Leu Ala Lys Leu
    290                 295                 300

cgc aac cgt att ccc ggc atg ttg atc acc cgg atc agg cgg ggt gac      960
Arg Asn Arg Ile Pro Gly Met Leu Ile Thr Arg Ile Arg Arg Gly Asp
305                 310                 315                 320

acc gac ctg att gcg cat ccg gat atg acc ctc cag ctg ggt gat ctg     1008
Thr Asp Leu Ile Ala His Pro Asp Met Thr Leu Gln Leu Gly Asp Leu
                325                 330                 335

gtc cgc gtg gtt gcc ccc gcc gag cgg atc aag gag gcc acc cac atc     1056
Val Arg Val Val Ala Pro Ala Glu Arg Ile Lys Glu Ala Thr His Ile
            340                 345                 350

ttc ggt gac tcc tac aaa cgc ctc gct gat ttc aat ctg gtt ccc ctg     1104
Phe Gly Asp Ser Tyr Lys Arg Leu Ala Asp Phe Asn Leu Val Pro Leu
        355                 360                 365

gtg gtc ggt ctc tcc ctc ggg gtg ctg gtg ggc atg atg gaa ttc ccc     1152
Val Val Gly Leu Ser Leu Gly Val Leu Val Gly Met Met Glu Phe Pro
    370                 375                 380

ctg ccc ggt gga agc gcc ctg tcc ctg ggc aat gcc ggt ggg ccc ctg     1200
Leu Pro Gly Gly Ser Ala Leu Ser Leu Gly Asn Ala Gly Gly Pro Leu
385                 390                 395                 400

ttg atc gcg ctg ctg ctg ggg gcg atg ggc cgc acc ggc aag gtg gtc     1248
Leu Ile Ala Leu Leu Leu Gly Ala Met Gly Arg Thr Gly Lys Val Val
                405                 410                 415

tgg cag atc ccc tac agt gcc aac ctc gcc ctc cga cag ctg ggc atc     1296
Trp Gln Ile Pro Tyr Ser Ala Asn Leu Ala Leu Arg Gln Leu Gly Ile
            420                 425                 430

acc atg ttt ctg gcg gcc atc ggg acg acc gcg ggt gcc ggg ttc cgg     1344
Thr Met Phe Leu Ala Ala Ile Gly Thr Thr Ala Gly Ala Gly Phe Arg
        435                 440                 445

tcc gcg ctg agc gat ccg gcc tcc ctg ctg atc atc ggg gtg ggt gcc     1392
Ser Ala Leu Ser Asp Pro Ala Ser Leu Leu Ile Ile Gly Val Gly Ala
    450                 455                 460

ctg ctg acc ctg gtg atc tcc gtg ctg gtt ctt gtc atc ggg cac aag     1440
Leu Leu Thr Leu Val Ile Ser Val Leu Val Leu Val Ile Gly His Lys
465                 470                 475                 480

gtc atg cgt atc ccc ttc ggc gag acc gcc ggc atc ctc gcc ggc acc     1488
Val Met Arg Ile Pro Phe Gly Glu Thr Ala Gly Ile Leu Ala Gly Thr
                485                 490                 495
```

-continued

```
cag acc cat cct gcg gtg ttg agc tac ata tcg gag gcc tcg cgc aat      1536
Gln Thr His Pro Ala Val Leu Ser Tyr Ile Ser Glu Ala Ser Arg Asn
            500                 505                 510

gaa ctg ccg gcg atg ggt tac acc tcc gtc tat ccc ctc gcc atg gtg      1584
Glu Leu Pro Ala Met Gly Tyr Thr Ser Val Tyr Pro Leu Ala Met Val
        515                 520                 525

gcg aag atc atc gcc gca cag gtg ctg ttg ttc ctg ctg ata tag          1629
Ala Lys Ile Ile Ala Ala Gln Val Leu Leu Phe Leu Leu Ile
    530                 535                 540


<210> SEQ ID NO 20
<211> LENGTH: 542
<212> TYPE: PRT
<213> ORGANISM: Corynebacterium accolens

<400> SEQUENCE: 20

Met Ser Ile Phe Val Glu Asn Gln Leu Leu Ala Leu Val Ala Ile Met
1               5                   10                  15

Gly Ile Gly Leu Leu Leu Gly Arg Ile Arg Phe Phe Gly Phe Arg Leu
            20                  25                  30

Gly Val Ala Ala Val Leu Phe Val Gly Leu Ala Phe Ser Thr Ile Glu
        35                  40                  45

Pro Asp Ile Thr Val Pro Pro Leu Ile Tyr Val Val Gly Leu Ala Leu
    50                  55                  60

Phe Val Tyr Thr Ile Gly Leu Glu Ala Gly Arg Asp Phe Phe Arg Ser
65                  70                  75                  80

Leu Arg Ser Thr Gly Leu Arg Asn Asn Gly Leu Ala Leu Gly Ala Ile
                85                  90                  95

Ile Ala Thr Thr Ala Ile Ala Trp Val Val Ile Lys Ala Leu Gly Leu
            100                 105                 110

Ala Pro Ala Thr Gly Ala Gly Met Leu Thr Gly Ala Leu Thr Asn Thr
        115                 120                 125

Pro Ala Met Ala Ala Val Val Asp Ala Leu Pro Ala Leu Ile Asp Asp
    130                 135                 140

Asn Pro Thr Asp Ala Ala Arg Ile Leu Glu Leu Pro Val Val Ala Tyr
145                 150                 155                 160

Ser Leu Thr Tyr Pro Leu Gly Val Leu Val Val Ile Leu Thr Ile Ala
                165                 170                 175

Val Cys Gly Gly Leu Phe Lys Val Asn His Glu Lys Glu Ala Lys Asn
            180                 185                 190

Ala Gly Val Ala Val Gln Glu Leu Thr Gly Arg Arg Val Arg Val Thr
        195                 200                 205

Arg Asp Asp Leu Pro Ala Ile Ser Asn Ile Pro Glu Leu Leu Asp Leu
    210                 215                 220

Glu Val Ile Val Ser Arg Val Glu Arg Arg Gly Gln His Asp Gln Phe
225                 230                 235                 240

Ile Pro Glu Glu Gly Asp Arg Thr Arg Leu Gly Asp Ile Leu Thr Val
                245                 250                 255

Val Gly Ser Asp Asp Glu Leu Glu Arg Ala Val Gly Leu Leu Gly Glu
            260                 265                 270

Phe Val Asp Gly His Pro Tyr Ser Asp Ile Asp Leu Asp Tyr Arg Arg
        275                 280                 285

Ile Phe Val Ser Asp Glu Ser Met Val Gly Val Pro Leu Ala Lys Leu
    290                 295                 300

Arg Asn Arg Ile Pro Gly Met Leu Ile Thr Arg Ile Arg Arg Gly Asp
305                 310                 315                 320
```

-continued

```
Thr Asp Leu Ile Ala His Pro Asp Met Thr Leu Gln Leu Gly Asp Leu
                325                 330                 335

Val Arg Val Val Ala Pro Ala Glu Arg Ile Lys Glu Ala Thr His Ile
            340                 345                 350

Phe Gly Asp Ser Tyr Lys Arg Leu Ala Asp Phe Asn Leu Val Pro Leu
        355                 360                 365

Val Val Gly Leu Ser Leu Gly Val Leu Val Gly Met Met Glu Phe Pro
    370                 375                 380

Leu Pro Gly Gly Ser Ala Leu Ser Leu Gly Asn Ala Gly Gly Pro Leu
385                 390                 395                 400

Leu Ile Ala Leu Leu Leu Gly Ala Met Gly Arg Thr Gly Lys Val Val
                405                 410                 415

Trp Gln Ile Pro Tyr Ser Ala Asn Leu Ala Leu Arg Gln Leu Gly Ile
            420                 425                 430

Thr Met Phe Leu Ala Ala Ile Gly Thr Thr Ala Gly Ala Gly Phe Arg
        435                 440                 445

Ser Ala Leu Ser Asp Pro Ala Ser Leu Leu Ile Ile Gly Val Gly Ala
    450                 455                 460

Leu Leu Thr Leu Val Ile Ser Val Leu Val Leu Val Ile Gly His Lys
465                 470                 475                 480

Val Met Arg Ile Pro Phe Gly Glu Thr Ala Gly Ile Leu Ala Gly Thr
                485                 490                 495

Gln Thr His Pro Ala Val Leu Ser Tyr Ile Ser Glu Ala Ser Arg Asn
            500                 505                 510

Glu Leu Pro Ala Met Gly Tyr Thr Ser Val Tyr Pro Leu Ala Met Val
        515                 520                 525

Ala Lys Ile Ile Ala Ala Gln Val Leu Leu Phe Leu Leu Ile
    530                 535                 540


<210> SEQ ID NO 21
<211> LENGTH: 3423
<212> TYPE: DNA
<213> ORGANISM: Brevibacterium flavum
<220> FEATURE:
<221> NAME/KEY: CDS
<222> LOCATION: (1)..(3420)

<400> SEQUENCE: 21

atg tcg act cac aca tct tca acg ctt cca gca ttc aaa aag atc ttg       48
Met Ser Thr His Thr Ser Ser Thr Leu Pro Ala Phe Lys Lys Ile Leu
1               5                   10                  15

gta gca aac cgc ggc gaa atc gcg gtc cgt gct ttc cgt gca gca ctc       96
Val Ala Asn Arg Gly Glu Ile Ala Val Arg Ala Phe Arg Ala Ala Leu
            20                  25                  30

gaa acc ggt gca gcc acg gta gct att tac ccc cgt gaa gat cgg gga      144
Glu Thr Gly Ala Ala Thr Val Ala Ile Tyr Pro Arg Glu Asp Arg Gly
        35                  40                  45

tca ttc cac cgc tct ttt gct tct gaa gct gtc cgc att ggt act gaa      192
Ser Phe His Arg Ser Phe Ala Ser Glu Ala Val Arg Ile Gly Thr Glu
    50                  55                  60

ggc tca cca gtc aag gcg tac ctg gac atc gat gaa att atc ggt gca      240
Gly Ser Pro Val Lys Ala Tyr Leu Asp Ile Asp Glu Ile Ile Gly Ala
65                  70                  75                  80

gct aaa aaa gtt aaa gca gat gct att tac ccg gga tat ggc ttc ctg      288
Ala Lys Lys Val Lys Ala Asp Ala Ile Tyr Pro Gly Tyr Gly Phe Leu
                85                  90                  95
```

-continued

```
tct gaa aat gcc cag ctt gcc cgc gag tgc gcg gaa aac ggc att act      336
Ser Glu Asn Ala Gln Leu Ala Arg Glu Cys Ala Glu Asn Gly Ile Thr
            100                 105                 110

ttt att ggc cca acc cca gag gtt ctt gat ctc acc ggt gat aag tct      384
Phe Ile Gly Pro Thr Pro Glu Val Leu Asp Leu Thr Gly Asp Lys Ser
        115                 120                 125

cgt gcg gta acc gcc gcg aag aag gct ggt ctg cca gtt ttg gcg gaa      432
Arg Ala Val Thr Ala Ala Lys Lys Ala Gly Leu Pro Val Leu Ala Glu
    130                 135                 140

tcc acc ccg agc aaa aac atc gat gac atc gtt aaa agc gct gaa ggc      480
Ser Thr Pro Ser Lys Asn Ile Asp Asp Ile Val Lys Ser Ala Glu Gly
145                 150                 155                 160

cag act tac ccc atc ttt gta aag gca gtt gcc ggt ggt ggc gga cgc      528
Gln Thr Tyr Pro Ile Phe Val Lys Ala Val Ala Gly Gly Gly Gly Arg
                165                 170                 175

ggt atg cgc ttt gtt tct tca cct gat gag ctt cgc aaa ttg gca aca      576
Gly Met Arg Phe Val Ser Ser Pro Asp Glu Leu Arg Lys Leu Ala Thr
            180                 185                 190

gaa gca tct cgt gaa gct gaa gcg gca ttc ggc gac ggt tcg gta tat      624
Glu Ala Ser Arg Glu Ala Glu Ala Ala Phe Gly Asp Gly Ser Val Tyr
        195                 200                 205

gtc gag cgt gct gtg att aac ccc cag cac att gaa gtg cag atc ctt      672
Val Glu Arg Ala Val Ile Asn Pro Gln His Ile Glu Val Gln Ile Leu
    210                 215                 220

ggc gat cgc act gga gaa gtt gta cac ctt tat gaa cgt gac tgc tca      720
Gly Asp Arg Thr Gly Glu Val Val His Leu Tyr Glu Arg Asp Cys Ser
225                 230                 235                 240

ctg cag cgt cgt cac caa aaa gtt gtc gaa att gcg cca gca cag cat      768
Leu Gln Arg Arg His Gln Lys Val Val Glu Ile Ala Pro Ala Gln His
                245                 250                 255

ttg gat cca gaa ctg cgt gat cgc att tgt gcg gat gca gta aag ttc      816
Leu Asp Pro Glu Leu Arg Asp Arg Ile Cys Ala Asp Ala Val Lys Phe
            260                 265                 270

tgc cgc tcc att ggt tac cag ggc gcg gga act gtg gaa ttc ttg gtc      864
Cys Arg Ser Ile Gly Tyr Gln Gly Ala Gly Thr Val Glu Phe Leu Val
        275                 280                 285

gat gaa aag ggc aac cac gtt ttc atc gaa atg aac cca cgt atc cag      912
Asp Glu Lys Gly Asn His Val Phe Ile Glu Met Asn Pro Arg Ile Gln
    290                 295                 300

gtt gag cac acc gtg act gaa gaa gtc acc gag gtg gac ctg gtg aag      960
Val Glu His Thr Val Thr Glu Glu Val Thr Glu Val Asp Leu Val Lys
305                 310                 315                 320

gcg cag atg cgc ttg gct gct ggt gca acc ttg aag gaa ttg ggt ctg     1008
Ala Gln Met Arg Leu Ala Ala Gly Ala Thr Leu Lys Glu Leu Gly Leu
                325                 330                 335

acc caa gat aag atc aag acc cac ggt gcg gca ctg cag tgc cgc atc     1056
Thr Gln Asp Lys Ile Lys Thr His Gly Ala Ala Leu Gln Cys Arg Ile
            340                 345                 350

acc acg gaa gat cca aac aac ggc ttc cgc cca gat acc gga act atc     1104
Thr Thr Glu Asp Pro Asn Asn Gly Phe Arg Pro Asp Thr Gly Thr Ile
        355                 360                 365

acc gcg tac cgc tca cca ggc gga gct ggc gtt cgt ctt gac ggt gca     1152
Thr Ala Tyr Arg Ser Pro Gly Gly Ala Gly Val Arg Leu Asp Gly Ala
    370                 375                 380

gct cag ctc ggt ggc gaa atc acc gca cac ttt gac tcc atg ctg gtg     1200
Ala Gln Leu Gly Gly Glu Ile Thr Ala His Phe Asp Ser Met Leu Val
385                 390                 395                 400

aaa atg acc tgc cgt ggt tcc gat ttt gaa act gct gtt gct cgt gca     1248
Lys Met Thr Cys Arg Gly Ser Asp Phe Glu Thr Ala Val Ala Arg Ala
                405                 410                 415
```

-continued

```
cag cgc gcg ttg gct gag ttc acc gtg tct ggt gtt gca acc aac att      1296
Gln Arg Ala Leu Ala Glu Phe Thr Val Ser Gly Val Ala Thr Asn Ile
            420                 425                 430

ggt ttc ttg cgt gcg ttg ctg cgt gaa gag gac ttt act tcc aag cgc      1344
Gly Phe Leu Arg Ala Leu Leu Arg Glu Glu Asp Phe Thr Ser Lys Arg
        435                 440                 445

atc gcc acc gga ttt atc ggc gat cac cca cac ctc ctt cag gct cca      1392
Ile Ala Thr Gly Phe Ile Gly Asp His Pro His Leu Leu Gln Ala Pro
    450                 455                 460

cct gcg gat gat gag cag gga cgc atc ctg gat tac ttg gca gat gtc      1440
Pro Ala Asp Asp Glu Gln Gly Arg Ile Leu Asp Tyr Leu Ala Asp Val
465                 470                 475                 480

acc gtg aac aag cct cat ggt gtg cgt cca aag gat gtt gca gca cca      1488
Thr Val Asn Lys Pro His Gly Val Arg Pro Lys Asp Val Ala Ala Pro
                485                 490                 495

atc gat aag ctg ccc aac atc aag gat ctg cca ctg cca cgc ggt tcc      1536
Ile Asp Lys Leu Pro Asn Ile Lys Asp Leu Pro Leu Pro Arg Gly Ser
            500                 505                 510

cgt gac cgc ctg aag cag ctt gga cca gca gcg ttt gcc cgc gat ctc      1584
Arg Asp Arg Leu Lys Gln Leu Gly Pro Ala Ala Phe Ala Arg Asp Leu
        515                 520                 525

cgt gag cag gac gca ctg gca gtt act gat acc acc ttc cgc gat gca      1632
Arg Glu Gln Asp Ala Leu Ala Val Thr Asp Thr Thr Phe Arg Asp Ala
    530                 535                 540

cac cag tct ttg ctt gcg acc cga gtc cgc tca ttc gca ctg aag cct      1680
His Gln Ser Leu Leu Ala Thr Arg Val Arg Ser Phe Ala Leu Lys Pro
545                 550                 555                 560

gcg gca gag gcc gtc gca aag ctg act cct gag ctt ttg tcc gtg gag      1728
Ala Ala Glu Ala Val Ala Lys Leu Thr Pro Glu Leu Leu Ser Val Glu
                565                 570                 575

gcc tgg ggc ggt gcg acc tac gat gtg gcg atg cgt ttc ctc ttt gag      1776
Ala Trp Gly Gly Ala Thr Tyr Asp Val Ala Met Arg Phe Leu Phe Glu
            580                 585                 590

gat ccg tgg gac agg ctc gac gag ctg cgc gag gcg atg ccg aat gtg      1824
Asp Pro Trp Asp Arg Leu Asp Glu Leu Arg Glu Ala Met Pro Asn Val
        595                 600                 605

aac att cag atg ctg ctt cgc ggc cgc aac acc gtg gga tac acc cca      1872
Asn Ile Gln Met Leu Leu Arg Gly Arg Asn Thr Val Gly Tyr Thr Pro
    610                 615                 620

tac cca gac tcc gtc tgt cgc gcg ttt gtt aag gaa gct gcc acc tcc      1920
Tyr Pro Asp Ser Val Cys Arg Ala Phe Val Lys Glu Ala Ala Thr Ser
625                 630                 635                 640

ggc gtg gac atc ttc cgc atc ttc gac gcg ctt aac gac gtc tcc cag      1968
Gly Val Asp Ile Phe Arg Ile Phe Asp Ala Leu Asn Asp Val Ser Gln
                645                 650                 655

atg cgt cca gca atc gac gca gtc ctg gag acc aac acc gcg gtc gct      2016
Met Arg Pro Ala Ile Asp Ala Val Leu Glu Thr Asn Thr Ala Val Ala
            660                 665                 670

gaa gtg gct atg gct tat tct ggt gat ctt tcc gat ccg aat gaa aag      2064
Glu Val Ala Met Ala Tyr Ser Gly Asp Leu Ser Asp Pro Asn Glu Lys
        675                 680                 685

ctc tac acc ctg gat tac tac ctg aag atg gca gag gag atc gtc aag      2112
Leu Tyr Thr Leu Asp Tyr Tyr Leu Lys Met Ala Glu Glu Ile Val Lys
    690                 695                 700

tct ggc gct cac att ctg gct att aag gat atg gct ggt ctg ctt cgc      2160
Ser Gly Ala His Ile Leu Ala Ile Lys Asp Met Ala Gly Leu Leu Arg
705                 710                 715                 720

cca gct gca gcc acc aag ctg gtc acc gca ctg cgc cgt gaa ttt gat      2208
Pro Ala Ala Ala Thr Lys Leu Val Thr Ala Leu Arg Arg Glu Phe Asp
                725                 730                 735
```

-continued

```
ctg cca gtg cac gtg cac acc cac gac act gcg ggt ggc cag ctg gca      2256
Leu Pro Val His Val His Thr His Asp Thr Ala Gly Gly Gln Leu Ala
            740                 745                 750

acc tac ttt gct gca gct caa gct ggt gca gat gct gtt gac ggt gct      2304
Thr Tyr Phe Ala Ala Ala Gln Ala Gly Ala Asp Ala Val Asp Gly Ala
        755                 760                 765

tcc gca cca ctg tct ggc acc acc tcc cag cca tcc ctg tct gcc att      2352
Ser Ala Pro Leu Ser Gly Thr Thr Ser Gln Pro Ser Leu Ser Ala Ile
    770                 775                 780

gtt gct gca ttc gcg cac acc cgt cgc gat acc ggt ttg agc ctc gag      2400
Val Ala Ala Phe Ala His Thr Arg Arg Asp Thr Gly Leu Ser Leu Glu
785                 790                 795                 800

gct gtt tct gac ctc gag cca tac tgg gaa gca gtg cgc gga ctg tac      2448
Ala Val Ser Asp Leu Glu Pro Tyr Trp Glu Ala Val Arg Gly Leu Tyr
                805                 810                 815

ctg cca ttt gag tct gga acc cca ggc cca acc ggt cgc gtc tac cgc      2496
Leu Pro Phe Glu Ser Gly Thr Pro Gly Pro Thr Gly Arg Val Tyr Arg
            820                 825                 830

cac gaa atc cca ggc gga cag ctg tcc aac ctg cgt gca cag gcc acc      2544
His Glu Ile Pro Gly Gly Gln Leu Ser Asn Leu Arg Ala Gln Ala Thr
        835                 840                 845

gca ctg ggc ctt gcg gat cgt ttc gaa ctc atc gaa gac aac tac gcg      2592
Ala Leu Gly Leu Ala Asp Arg Phe Glu Leu Ile Glu Asp Asn Tyr Ala
    850                 855                 860

gca gtt aat gag atg ctg gga cgc cca acc aag gtc acc cca tcc tcc      2640
Ala Val Asn Glu Met Leu Gly Arg Pro Thr Lys Val Thr Pro Ser Ser
865                 870                 875                 880

aag gtt gtt ggc gac ctc gca ctc cac ctc gtt ggt gcg ggt gtg gat      2688
Lys Val Val Gly Asp Leu Ala Leu His Leu Val Gly Ala Gly Val Asp
                885                 890                 895

cca gca gac ttt gct gca gat cca caa aag tac gac atc cca gac tct      2736
Pro Ala Asp Phe Ala Ala Asp Pro Gln Lys Tyr Asp Ile Pro Asp Ser
            900                 905                 910

gtc atc gcg ttc ctg cgc ggc gag ctt ggt aac cct cca ggt ggc tgg      2784
Val Ile Ala Phe Leu Arg Gly Glu Leu Gly Asn Pro Pro Gly Gly Trp
        915                 920                 925

cca gag cca ctg cgc acc cgc gca ctg gaa ggc cgc tcc gaa ggc aag      2832
Pro Glu Pro Leu Arg Thr Arg Ala Leu Glu Gly Arg Ser Glu Gly Lys
    930                 935                 940

gca cct ctg acg gaa gtt cct gag gaa gag cag gcg cac ctc gac gct      2880
Ala Pro Leu Thr Glu Val Pro Glu Glu Glu Gln Ala His Leu Asp Ala
945                 950                 955                 960

gat gat tcc aag gaa cgt cgc aac agc ctc aac cgc ctg ctg ttc ccg      2928
Asp Asp Ser Lys Glu Arg Arg Asn Ser Leu Asn Arg Leu Leu Phe Pro
                965                 970                 975

aag cca acc gaa gag ttc ctc gag cac cgt cgc cgc ttc ggc aac acc      2976
Lys Pro Thr Glu Glu Phe Leu Glu His Arg Arg Arg Phe Gly Asn Thr
            980                 985                 990

tct gcg ctg gat gat cgt gaa ttc  ttc tac ggc ctg gtc  gaa ggc cgc    3024
Ser Ala Leu Asp Asp Arg Glu Phe  Phe Tyr Gly Leu Val  Glu Gly Arg
        995                 1000                1005

gag act  ttg atc cgc ctg cca  gat gtg cgc acc cca  ctg ctt gtt      3069
Glu Thr  Leu Ile Arg Leu Pro  Asp Val Arg Thr Pro  Leu Leu Val
    1010                 1015                 1020

cgc ctg  gat gcg atc tcc gag  cca gac gat aag ggt  atg cgc aat      3114
Arg Leu  Asp Ala Ile Ser Glu  Pro Asp Asp Lys Gly  Met Arg Asn
    1025                 1030                 1035

gtt gtg  gcc aac gtc aac ggc  cag atc cgc cca atg  cgt gtg cgt      3159
Val Val  Ala Asn Val Asn Gly  Gln Ile Arg Pro Met  Arg Val Arg
    1040                 1045                 1050
```

-continued

```
gac cgc  tcc gtt gag tct gtc  acc gca acc gca gaa  aag gca gat      3204
Asp Arg  Ser Val Glu Ser Val  Thr Ala Thr Ala Glu  Lys Ala Asp
    1055                 1060                 1065

tcc tcc  aac aag ggc cat gtt  gct gca cca ttc gct  ggt gtt gtc      3249
Ser Ser  Asn Lys Gly His Val  Ala Ala Pro Phe Ala  Gly Val Val
    1070                 1075                 1080

act gtg  act gtt gct gaa ggt  gat gag gtc aag gct  gga gat gca      3294
Thr Val  Thr Val Ala Glu Gly  Asp Glu Val Lys Ala  Gly Asp Ala
    1085                 1090                 1095

gtc gca  atc atc gag gct atg  aag atg gaa gca aca  atc act gct      3339
Val Ala  Ile Ile Glu Ala Met  Lys Met Glu Ala Thr  Ile Thr Ala
    1100                 1105                 1110

tct gtt  gac ggc aaa atc gat  cgc gtt gtg gtt cct  gct gca acg      3384
Ser Val  Asp Gly Lys Ile Asp  Arg Val Val Val Pro  Ala Ala Thr
    1115                 1120                 1125

aag gtg  gaa ggt ggc gac ttg  atc gtc gtc gtt tcc  taa              3423
Lys Val  Glu Gly Gly Asp Leu  Ile Val Val Val Ser
    1130                 1135                 1140
```

<210> SEQ ID NO 22
<211> LENGTH: 1140
<212> TYPE: PRT
<213> ORGANISM: Brevibacterium flavum

<400> SEQUENCE: 22

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Asp Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ser Ser Pro Asp Glu Leu Arg Lys Leu Ala Thr
            180                 185                 190

Glu Ala Ser Arg Glu Ala Glu Ala Ala Phe Gly Asp Gly Ser Val Tyr
        195                 200                 205

Val Glu Arg Ala Val Ile Asn Pro Gln His Ile Glu Val Gln Ile Leu
    210                 215                 220

Gly Asp Arg Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255
```

-continued

```
Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Gly Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670
```

-continued

Glu Val Ala Met Ala Tyr Ser Gly Asp Leu Ser Asp Pro Asn Glu Lys
675 680 685

Leu Tyr Thr Leu Asp Tyr Tyr Leu Lys Met Ala Glu Glu Ile Val Lys
690 695 700

Ser Gly Ala His Ile Leu Ala Ile Lys Asp Met Ala Gly Leu Leu Arg
705 710 715 720

Pro Ala Ala Ala Thr Lys Leu Val Thr Ala Leu Arg Arg Glu Phe Asp
725 730 735

Leu Pro Val His Val His Thr His Asp Thr Ala Gly Gly Gln Leu Ala
740 745 750

Thr Tyr Phe Ala Ala Ala Gln Ala Gly Ala Asp Ala Val Asp Gly Ala
755 760 765

Ser Ala Pro Leu Ser Gly Thr Thr Ser Gln Pro Ser Leu Ser Ala Ile
770 775 780

Val Ala Ala Phe Ala His Thr Arg Arg Asp Thr Gly Leu Ser Leu Glu
785 790 795 800

Ala Val Ser Asp Leu Glu Pro Tyr Trp Glu Ala Val Arg Gly Leu Tyr
805 810 815

Leu Pro Phe Glu Ser Gly Thr Pro Gly Pro Thr Gly Arg Val Tyr Arg
820 825 830

His Glu Ile Pro Gly Gly Gln Leu Ser Asn Leu Arg Ala Gln Ala Thr
835 840 845

Ala Leu Gly Leu Ala Asp Arg Phe Glu Leu Ile Glu Asp Asn Tyr Ala
850 855 860

Ala Val Asn Glu Met Leu Gly Arg Pro Thr Lys Val Thr Pro Ser Ser
865 870 875 880

Lys Val Val Gly Asp Leu Ala Leu His Leu Val Gly Ala Gly Val Asp
885 890 895

Pro Ala Asp Phe Ala Ala Asp Pro Gln Lys Tyr Asp Ile Pro Asp Ser
900 905 910

Val Ile Ala Phe Leu Arg Gly Glu Leu Gly Asn Pro Pro Gly Gly Trp
915 920 925

Pro Glu Pro Leu Arg Thr Arg Ala Leu Glu Gly Arg Ser Glu Gly Lys
930 935 940

Ala Pro Leu Thr Glu Val Pro Glu Glu Glu Gln Ala His Leu Asp Ala
945 950 955 960

Asp Asp Ser Lys Glu Arg Arg Asn Ser Leu Asn Arg Leu Leu Phe Pro
965 970 975

Lys Pro Thr Glu Glu Phe Leu Glu His Arg Arg Arg Phe Gly Asn Thr
980 985 990

Ser Ala Leu Asp Asp Arg Glu Phe Phe Tyr Gly Leu Val Glu Gly Arg
995 1000 1005

Glu Thr Leu Ile Arg Leu Pro Asp Val Arg Thr Pro Leu Leu Val
1010 1015 1020

Arg Leu Asp Ala Ile Ser Glu Pro Asp Asp Lys Gly Met Arg Asn
1025 1030 1035

Val Val Ala Asn Val Asn Gly Gln Ile Arg Pro Met Arg Val Arg
1040 1045 1050

Asp Arg Ser Val Glu Ser Val Thr Ala Thr Ala Glu Lys Ala Asp
1055 1060 1065

Ser Ser Asn Lys Gly His Val Ala Ala Pro Phe Ala Gly Val Val
1070 1075 1080

-continued

```
Thr Val  Thr Val Ala Glu Gly  Asp Glu Val Lys Ala  Gly Asp Ala
    1085                1090                1095

Val Ala  Ile Ile Glu Ala Met  Lys Met Glu Ala Thr  Ile Thr Ala
    1100                1105                1110

Ser Val  Asp Gly Lys Ile Asp  Arg Val Val Val Pro  Ala Ala Thr
    1115                1120                1125

Lys Val  Glu Gly Gly Asp Leu  Ile Val Val Val Ser
    1130                1135                1140


<210> SEQ ID NO 23
<211> LENGTH: 1626
<212> TYPE: DNA
<213> ORGANISM: Corynebacterium diphtheriae
<220> FEATURE:
<221> NAME/KEY: CDS
<222> LOCATION: (1)..(1626)

<400> SEQUENCE: 23

gtg gat atc ttc gtg gca aac ccg ctg ttg gcg ctt ttt gtc atc atg       48
Val Asp Ile Phe Val Ala Asn Pro Leu Leu Ala Leu Phe Val Ile Met
1               5                   10                  15

gcg gtt gga tta gcg atc ggt cag gtt aaa atc cga ggt ttt agt ctc       96
Ala Val Gly Leu Ala Ile Gly Gln Val Lys Ile Arg Gly Phe Ser Leu
            20                  25                  30

gga gtg gca gca gtg ctt ttt gca ggc gtt gga ttt gcg gct gta gag      144
Gly Val Ala Ala Val Leu Phe Ala Gly Val Gly Phe Ala Ala Val Glu
        35                  40                  45

cct gat att cac atc cca cac ttg gtg tac atc ttg gga ttg tct att      192
Pro Asp Ile His Ile Pro His Leu Val Tyr Ile Leu Gly Leu Ser Ile
    50                  55                  60

ttt gtg tac tcc atc ggt ttg gaa tca ggc cat gcg ttt ttc gcc ctg      240
Phe Val Tyr Ser Ile Gly Leu Glu Ser Gly His Ala Phe Phe Ala Leu
65                  70                  75                  80

ttt aag tcg caa gga gtc aaa caa aac gcg ctc gct att acc gcg ttg      288
Phe Lys Ser Gln Gly Val Lys Gln Asn Ala Leu Ala Ile Thr Ala Leu
                85                  90                  95

gcg ctg ata aca ggc att tct atc gct ttg ttt tcg ctg ata cat ctc      336
Ala Leu Ile Thr Gly Ile Ser Ile Ala Leu Phe Ser Leu Ile His Leu
            100                 105                 110

aac ggg gtc acc gct gct ggg ttg ttt aca ggc gcg gta aca aat aca      384
Asn Gly Val Thr Ala Ala Gly Leu Phe Thr Gly Ala Val Thr Asn Thr
        115                 120                 125

ccg gcc atg gct gcc gtg gtg gat tcg tta ccc agc atc ttt ggg gat      432
Pro Ala Met Ala Ala Val Val Asp Ser Leu Pro Ser Ile Phe Gly Asp
    130                 135                 140

gcg aac aag gta cac gag gtg gaa tcg ttg ccc tta gtt gca tat tcg      480
Ala Asn Lys Val His Glu Val Glu Ser Leu Pro Leu Val Ala Tyr Ser
145                 150                 155                 160

ctg gcc tac ccc atc ggc gta ttg gga gtt atc gcg gca att ggg ttg      528
Leu Ala Tyr Pro Ile Gly Val Leu Gly Val Ile Ala Ala Ile Gly Leu
                165                 170                 175

tgt gca aag tgg ttc cgt atc gat cac gtg caa gaa gct cac gac gca      576
Cys Ala Lys Trp Phe Arg Ile Asp His Val Gln Glu Ala His Asp Ala
            180                 185                 190

ggt gtt gct gtt gag gat ttg ttc acc cgt cag atc aag gtc aat cat      624
Gly Val Ala Val Glu Asp Leu Phe Thr Arg Gln Ile Lys Val Asn His
        195                 200                 205

gtg gtt acg ggc tct gat ctt gtg att gat atc cac cac acg ctg ggc      672
Val Val Thr Gly Ser Asp Leu Val Ile Asp Ile His His Thr Leu Gly
    210                 215                 220
```

-continued

```
cta gag att att gtc tcg cga att gag cgt gat ggt cag cag act ctc      720
Leu Glu Ile Ile Val Ser Arg Ile Glu Arg Asp Gly Gln Gln Thr Leu
225                 230                 235                 240

cct act gcg tcg tct cgt atc cat atg gga gat gtg ttg tct gtg gtg      768
Pro Thr Ala Ser Ser Arg Ile His Met Gly Asp Val Leu Ser Val Val
                245                 250                 255

ggc acg gcc gag gaa ctc gac aag gcc gcg cat gtg cta ggt gat ttg      816
Gly Thr Ala Glu Glu Leu Asp Lys Ala Ala His Val Leu Gly Asp Leu
            260                 265                 270

ctc cca ggc gat cct ttc cat ggt cac gat tta gat tat cgg cgc att      864
Leu Pro Gly Asp Pro Phe His Gly His Asp Leu Asp Tyr Arg Arg Ile
        275                 280                 285

ttt gtt tcc aat cag gat tta gtg ggc ata cct ctg gct aaa ctt cgg      912
Phe Val Ser Asn Gln Asp Leu Val Gly Ile Pro Leu Ala Lys Leu Arg
    290                 295                 300

cct cga ttg tca gga att ttg att act cgg gtc cgt cgt ggc gac cat      960
Pro Arg Leu Ser Gly Ile Leu Ile Thr Arg Val Arg Arg Gly Asp His
305                 310                 315                 320

gac cat gtg gct act ccg gaa aca gtt ttg cag ctt ggc gac cgt gtt     1008
Asp His Val Ala Thr Pro Glu Thr Val Leu Gln Leu Gly Asp Arg Val
                325                 330                 335

cgg gtg gtg gca gct cat gat cgt atg aaa tcc gtg acg gca ctg ttc     1056
Arg Val Val Ala Ala His Asp Arg Met Lys Ser Val Thr Ala Leu Phe
            340                 345                 350

ggc gat tcc tat cgt cgc ctt tct gat ttc aat ctt ttc cct ctc gtt     1104
Gly Asp Ser Tyr Arg Arg Leu Ser Asp Phe Asn Leu Phe Pro Leu Val
        355                 360                 365

gcc ggg ctt gcg ctt gga ttg ctc gtt ggc atg att gag gta cca ctt     1152
Ala Gly Leu Ala Leu Gly Leu Leu Val Gly Met Ile Glu Val Pro Leu
    370                 375                 380

cct ggc ggt gct gcg ttg tct tta gga agc gcc ggc ggc cca tta gta     1200
Pro Gly Gly Ala Ala Leu Ser Leu Gly Ser Ala Gly Gly Pro Leu Val
385                 390                 395                 400

gta gct ctc gtt cta ggc gca gtg gga cgc tca ggt cgt ttt gtg tgg     1248
Val Ala Leu Val Leu Gly Ala Val Gly Arg Ser Gly Arg Phe Val Trp
                405                 410                 415

cag gtt cct tac gga gca aac ttg gca ctg cga caa cta ggc atc acc     1296
Gln Val Pro Tyr Gly Ala Asn Leu Ala Leu Arg Gln Leu Gly Ile Thr
            420                 425                 430

ttg ttt ctc gcc gct att ggt acc act gca gga gct agt ttc cgt gca     1344
Leu Phe Leu Ala Ala Ile Gly Thr Thr Ala Gly Ala Ser Phe Arg Ala
        435                 440                 445

tcg cta tca gat ccc gca tcg ttg acc atc att gcc gtt ggt gcc atc     1392
Ser Leu Ser Asp Pro Ala Ser Leu Thr Ile Ile Ala Val Gly Ala Ile
    450                 455                 460

atc acc ttg aca ttg gct atc ttt gtt ctg gtt gtg ggc tat aag gtg     1440
Ile Thr Leu Thr Leu Ala Ile Phe Val Leu Val Val Gly Tyr Lys Val
465                 470                 475                 480

atg aag atc ccg tac ggc caa aca gcg ggc atg ctt gcg ggt att caa     1488
Met Lys Ile Pro Tyr Gly Gln Thr Ala Gly Met Leu Ala Gly Ile Gln
                485                 490                 495

acg cac cca gct gta ctg tcc tat gtt tct gcg atg acg aaa aat gat     1536
Thr His Pro Ala Val Leu Ser Tyr Val Ser Ala Met Thr Lys Asn Asp
            500                 505                 510

ctg ccg gca ttg ggc tac acc tcg gta tat cca ctg gcc atg atc gct     1584
Leu Pro Ala Leu Gly Tyr Thr Ser Val Tyr Pro Leu Ala Met Ile Ala
        515                 520                 525

aag atc att gca gca cag gtt gtg cta ttc gct ttg aca tag             1626
Lys Ile Ile Ala Ala Gln Val Val Leu Phe Ala Leu Thr
    530                 535                 540
```

-continued

<210> SEQ ID NO 24
<211> LENGTH: 541
<212> TYPE: PRT
<213> ORGANISM: Corynebacterium diphtheriae

<400> SEQUENCE: 24

Met Asp Ile Phe Val Ala Asn Pro Leu Leu Ala Leu Phe Val Ile Met
1 5 10 15

Ala Val Gly Leu Ala Ile Gly Gln Val Lys Ile Arg Gly Phe Ser Leu
20 25 30

Gly Val Ala Ala Val Leu Phe Ala Gly Val Gly Phe Ala Ala Val Glu
35 40 45

Pro Asp Ile His Ile Pro His Leu Val Tyr Ile Leu Gly Leu Ser Ile
50 55 60

Phe Val Tyr Ser Ile Gly Leu Glu Ser Gly His Ala Phe Phe Ala Leu
65 70 75 80

Phe Lys Ser Gln Gly Val Lys Gln Asn Ala Leu Ala Ile Thr Ala Leu
85 90 95

Ala Leu Ile Thr Gly Ile Ser Ile Ala Leu Phe Ser Leu Ile His Leu
100 105 110

Asn Gly Val Thr Ala Ala Gly Leu Phe Thr Gly Ala Val Thr Asn Thr
115 120 125

Pro Ala Met Ala Ala Val Val Asp Ser Leu Pro Ser Ile Phe Gly Asp
130 135 140

Ala Asn Lys Val His Glu Val Glu Ser Leu Pro Leu Val Ala Tyr Ser
145 150 155 160

Leu Ala Tyr Pro Ile Gly Val Leu Gly Val Ile Ala Ala Ile Gly Leu
165 170 175

Cys Ala Lys Trp Phe Arg Ile Asp His Val Gln Glu Ala His Asp Ala
180 185 190

Gly Val Ala Val Glu Asp Leu Phe Thr Arg Gln Ile Lys Val Asn His
195 200 205

Val Val Thr Gly Ser Asp Leu Val Ile Asp Ile His His Thr Leu Gly
210 215 220

Leu Glu Ile Ile Val Ser Arg Ile Glu Arg Asp Gly Gln Gln Thr Leu
225 230 235 240

Pro Thr Ala Ser Ser Arg Ile His Met Gly Asp Val Leu Ser Val Val
245 250 255

Gly Thr Ala Glu Glu Leu Asp Lys Ala Ala His Val Leu Gly Asp Leu
260 265 270

Leu Pro Gly Asp Pro Phe His Gly His Asp Leu Asp Tyr Arg Arg Ile
275 280 285

Phe Val Ser Asn Gln Asp Leu Val Gly Ile Pro Leu Ala Lys Leu Arg
290 295 300

Pro Arg Leu Ser Gly Ile Leu Ile Thr Arg Val Arg Arg Gly Asp His
305 310 315 320

Asp His Val Ala Thr Pro Glu Thr Val Leu Gln Leu Gly Asp Arg Val
325 330 335

Arg Val Val Ala Ala His Asp Arg Met Lys Ser Val Thr Ala Leu Phe
340 345 350

Gly Asp Ser Tyr Arg Arg Leu Ser Asp Phe Asn Leu Phe Pro Leu Val
355 360 365

Ala Gly Leu Ala Leu Gly Leu Leu Val Gly Met Ile Glu Val Pro Leu
370 375 380

-continued

```
Pro Gly Gly Ala Ala Leu Ser Leu Gly Ser Ala Gly Gly Pro Leu Val
385                 390                 395                 400

Val Ala Leu Val Leu Gly Ala Val Gly Arg Ser Gly Arg Phe Val Trp
                405                 410                 415

Gln Val Pro Tyr Gly Ala Asn Leu Ala Leu Arg Gln Leu Gly Ile Thr
            420                 425                 430

Leu Phe Leu Ala Ala Ile Gly Thr Thr Ala Gly Ala Ser Phe Arg Ala
        435                 440                 445

Ser Leu Ser Asp Pro Ala Ser Leu Thr Ile Ile Ala Val Gly Ala Ile
    450                 455                 460

Ile Thr Leu Thr Leu Ala Ile Phe Val Leu Val Val Gly Tyr Lys Val
465                 470                 475                 480

Met Lys Ile Pro Tyr Gly Gln Thr Ala Gly Met Leu Ala Gly Ile Gln
                485                 490                 495

Thr His Pro Ala Val Leu Ser Tyr Val Ser Ala Met Thr Lys Asn Asp
            500                 505                 510

Leu Pro Ala Leu Gly Tyr Thr Ser Val Tyr Pro Leu Ala Met Ile Ala
        515                 520                 525

Lys Ile Ile Ala Ala Gln Val Val Leu Phe Ala Leu Thr
    530                 535                 540
```